(12) United States Patent
Zhou et al.

(10) Patent No.: US 9,079,965 B2
(45) Date of Patent: Jul. 14, 2015

(54) BISPECIFIC ANTIBODY

(71) Applicant: WUHAN YZY BIOPHARMA CO., LTD., Wuhan (CN)

(72) Inventors: Pengfei Zhou, Hubei (CN); Jing Zhang, Hubei (CN); Yongxiang Yan, Hubei (CN)

(73) Assignee: Wuhan YZY Biopharma Co., LTD., Wuhan (CN)

( * ) Notice: Subject to any disclaimer, the term of this patent is extended or adjusted under 35 U.S.C. 154(b) by 0 days.

(21) Appl. No.: 14/209,708

(22) Filed: Mar. 13, 2014

(65) Prior Publication Data
US 2014/0243505 A1 Aug. 28, 2014

Related U.S. Application Data

(63) Continuation of application No. PCT/CN2012/084982, filed on Nov. 21, 2012.

(51) Int. Cl.
*C07K 16/28* (2006.01)
*C07K 16/30* (2006.01)
*C07K 16/46* (2006.01)
*C07K 16/32* (2006.01)

(52) U.S. Cl.
CPC ........... *C07K 16/468* (2013.01); *C07K 16/2809* (2013.01); *C07K 16/32* (2013.01); *C07K 2317/31* (2013.01); *C07K 2317/51* (2013.01); *C07K 2317/515* (2013.01); *C07K 2317/52* (2013.01); *C07K 2317/622* (2013.01); *C07K 2317/64* (2013.01); *C07K 2317/732* (2013.01); *C07K 2317/94* (2013.01)

(58) Field of Classification Search
CPC ........... C07K 2317/30; C07K 2317/31; C07K 2317/50–2317/55; C07K 2317/60–2317/64; C07K 2319/70; C07K 16/32; C07K 16/2806; C07K 16/468
See application file for complete search history.

(56) References Cited

U.S. PATENT DOCUMENTS

| | | | | |
|---|---|---|---|---|
| 2007/0287170 | A1* | 12/2007 | Davis et al. | 435/69.1 |
| 2008/0031874 | A1* | 2/2008 | Sanders | 424/133.1 |
| 2010/0286374 | A1* | 11/2010 | Kannan et al. | 530/387.3 |
| 2011/0217302 | A1* | 9/2011 | Odegard et al. | 424/134.1 |
| 2013/0058937 | A1* | 3/2013 | Auer et al. | 424/136.1 |
| 2013/0078249 | A1* | 3/2013 | Ast et al. | 424/136.1 |
| 2013/0078250 | A1* | 3/2013 | Ast et al. | 424/136.1 |
| 2013/0171095 | A1* | 7/2013 | Bernett et al. | 424/85.2 |
| 2014/0154253 | A1* | 6/2014 | Ng et al. | 424/136.1 |
| 2014/0170149 | A1* | 6/2014 | Neijssen et al. | 424/136.1 |

FOREIGN PATENT DOCUMENTS

| | | |
|---|---|---|
| WO | WO-2012/069466 A1 | 5/2012 |
| WO | WO-2012/123949 A1 | 9/2012 |
| WO | WO-2012/143524 A2 | 10/2012 |

OTHER PUBLICATIONS

Muda et al., Protein Eng. Design Selection, May 2011; 24(5):447-54.*
Annemiek V. van Spriel, et al., "Immunotherapeutic Perspective for Bispecific Antibodies", Immunology Today, Aug. 2000, vol. 21, No. 8, pp. 391-397, ISSN 0167-5699.
Ahmad, et al., "scFv antibody: Principles and clinical application", Clinical and Developmental Immunology, pp. 1-15, (2012).
Jin, et al., "The design and Engineering of IgG-Like bispecific antibodies", Bispecific Antibodies, Chapter 9, pp. 1-19, (2010).
International Search Report and Written Opinion for International Application No. PCT/CN2012/084982 dated Aug. 12, 2013.
Ridgway, et al., "Knobs-into-holes engineering of antibody $C_H3$ domains for heavy chain heterodimerization", Protein Engineering, vol. 9, No. 7, pp. 617-621, (1996).

* cited by examiner

*Primary Examiner* — Sheela J Huff
*Assistant Examiner* — Jessica H Roark
(74) *Attorney, Agent, or Firm* — Foley & Lardner LLP

(57) ABSTRACT

Provided are bispecific antibodies comprised of a single-chain unit having specificity to an immune cell and a monovalent unit having specificity to a tumor cell or a microorganism. The single-chain unit includes a single-chain variable fragment (scFv) fused to an Fc fragment and the monovalent unit includes a light chain and heavy chain pair. Also provided are methods of preparing bispecific antibodies and pharmaceutical and diagnostic uses of these antibodies.

8 Claims, 16 Drawing Sheets

A
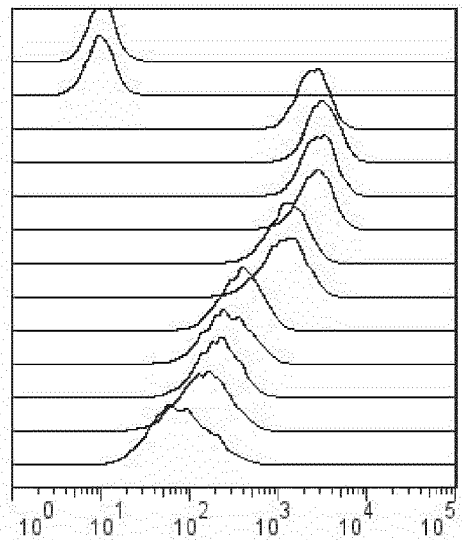

| SampleID | Mean, FL2-Log Height |
|---|---|
| negative control | 11.2 |
| human IgG(160nM) | 10.8 |
| Herceptin(20nM) | 2581 |
| MSBODY(160nM) | 3333 |
| MSBODY(80nM) | 3016 |
| MSBODY(40nM) | 2772 |
| MSBODY(20nM) | 1404 |
| MSBODY(10nM) | 1285 |
| MSBODY(5nM) | 428 |
| MSBODY(2.5nM) | 313 |
| MSBODY(1.25nM) | 236 |
| MSBODY(0.625nM) | 176 |
| MSBODY(0.3125nM) | 105 | anti-human IgG Fc-PE

B
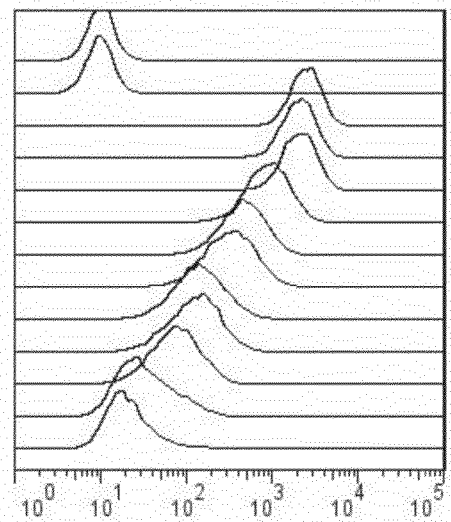

| SampleID | Mean, FL2-Log Height |
|---|---|
| negative control | 11.2 |
| human IgG(160nM) | 10.8 |
| Herceptin(20nM) | 2581 |
| SMBODY(160nM) | 2169 |
| SMBODY(80nM) | 2203 |
| SMBODY(40nM) | 1014 |
| SMBODY(20nM) | 528 |
| SMBODY(10nM) | 389 |
| SMBODY(5nM) | 175 |
| SMBODY(2.5nM) | 153 |
| SMBODY(1.25nM) | 90.3 |
| SMBODY(0.625nM) | 44.6 |
| SMBODY(0.3125nM) | 25.6 | anti-human IgG Fc-PE

SEQ ID NO: 1

QVQLQQSGAELARPGASVKMSCKASGYTFTRYTMHWVKQRPGQGLEWIGYINPSRGYTNYNQKFKDKATLT

TDKSSSTAYMQLSSLTSEDSAVYYCARYYDDHYCLDYWGQGTTLTVSSGGGGSGGGGSGGGGSQIVLTQSP

AIMSASPGEKVTMTCSASSSVSYMNWYQQKSGTSPKRWIYDTSKLASGVPAHFRGSGSGTSYSLTISGMEA

EDAATYYCQQWSSNPFTEGSGTKLEINRGAAAEPKSCDKTHTCPPCPAPELLGGPSVFLEPPKPKDTLMIS
216 231

RTPEVTCVVVDVSHEDPEVKFNWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPSDIAVEWESNGQPENNYKTTPP
341 L368R

VLDSDGSFFLYSKLTVDKSRWQQGNVFSCSVMHEALHNHYTQKSLSLSPGK
D399K   Y407A

FIG. 21

SEQ ID NO: 3

EVQLVESGGGLVQPGGSLRLSCAASGENIKDTYIHWVRQAPGKGLEWVARIYPTNGYTRYAD

SVKGRETISADTSKNTAYLQMNSLRAEDTAVYYCSRWGGDGFYAMDYWGQGTLVTVSSASTK
                                                                           118

GPSVFPLAPSSKSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAAPELLGGPSVFLEPP
                                216                    231

KPKDTLMISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELTKNQVSLTCLV
                                         341                                  T366W

KGFYPSDIAVEWESNGQPENNYKTTPPVLDSDGSFFLYSKLTVDKSRWQQGNVFSCSVMHEA
                      K392D                    K409D

LHNHYTQKSLSLSPGK

SEQUENCE LISTING

<160> NUMBER OF SEQ ID NOS: 52

<210> SEQ ID NO 1
<211> LENGTH: 477
<212> TYPE: PRT
<213> ORGANISM: Artificial Sequence
<220> FEATURE:
<223> OTHER INFORMATION: Synthetic

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240

Arg Gly Ala Ala Ala Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys

```
                 355                 360                 365
Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 2
<211> LENGTH: 1434
<212> TYPE: DNA
<213> ORGANISM: Artificial Sequence
<220> FEATURE:
<223> OTHER INFORMATION: Synthetic

<400> SEQUENCE: 2
caggtgcagc tggtgcagag cggcggcggc gtcgtgcagc cgggcaggtc cctgagactg      60
tcttgtaagg cttctggata caccttcact agatacacaa tgcactgggt cagacaggct     120
cctggaaagg gactcgagtg gattggatac attaatccta gcagaggtta ctactaactac    180 aatcagaagt ttaaggacag attcacaatt tctactgaca aatctaagag tacagccttc     240
ctgcagatgg actcactcag acctgaggat accggagtct attttgtgc tagatattac      300 gatgaccact actgtctgga ctactggggc aaggtacccc ggtcaccgt gagctcagga      360 ggcggcggtt caggcggagg tggaagtggt ggaggaggtt ctgatattca gatgacccag     420
agcccgtcaa gcttatctgc ttctgtcgga cagagtca caatcacatg ttctgcttct      480
agctctgtct cttacatgaa ctggtatcag cagacacctg aaaggctcc taagcggtgg     540 atctacgaca catctaagct cgcttctgga gtcccttcta gattctctgg ttctggctct    600
ggaacagact acacattcac aatctcttct ctccaacctg aggacatcgc tacatactac    660
tgccaacagt ggtctagcaa tccttcaca ttcggacagg gtaccaaact gcagatcaca     720
agaggtgcgg ccgcagagcc caaatcttgt gacaaaactc acacatgccc accgtgccca    780
gcacctgaac tcctgggggg accgtcagtc ttcctcttcc cccaaaaacc caaggacacc    840
ctcatgatct cccggacccc tgaggtcaca tgcgtggtgg tggacgtgag ccacgaagac    900
cctgaggtca agttcaactg gtacgtggac ggcgtggagg tgcataatgc caagacaaag    960
ccgcgggagg agcagtacaa cagcacgtac cgtgtggtca gcgtcctcac cgtcctgcac   1020
caggactggc tgaatggcaa ggagtacaag tgcaaggtct ccaacaaagc cctcccagcc   1080
cccatcgaga aaaccatctc caaagccaaa gggcagcccc gagaaccaca ggtgtacacc   1140 ctgccccat cccgggatga gctgaccaag aaccaggtca gcctgacctg cctggtcaaa    1200
ggcttctatc ccagcgacat cgccgtggag tgggagagca atgggcagcc ggagaacaac   1260
tacaagacca cgcctcccgt gctggactcc gacggctcct tcttcctcta cagcaagctc   1320
accgtggaca agagcaggtg gcagcagggg aacgtcttct catgctccgt gatgcatgag   1380
```
gctctgcaca accactacac gcagaagagc ctctccctgt ctccgggtaa atga    1434

<210> SEQ ID NO 3
<211> LENGTH: 450
<212> TYPE: PRT
<213> ORGANISM: Artificial Sequence
<220> FEATURE:
<223> OTHER INFORMATION: Synthetic

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu

```
                355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 4
<211> LENGTH: 1353
<212> TYPE: DNA
<213> ORGANISM: Artificial Sequence
<220> FEATURE:
<223> OTHER INFORMATION: Synthetic

<400> SEQUENCE: 4
gaagtgcagc tggtggaaag cggcggcggc ctggtgcagc cgggcggatc cctgcgcctg      60
agctgcgcgg cgagcggctt taacattaaa gataccta ttcattgggt gcgccaggcg      120
ccgggcaaag gcctggaatg gtggcgcgc atttatccga ccaacggcta tacccgctat     180
gcggatagcg tgaaaggccg ctttaccatt agcgcggata ccagcaaaaa caccgcgtat    240
ctgcagatga acagcctgcg cgcggaagat accgcggtgt attattgcag ccgctggggc    300
ggcgatggct tttatgcgat ggattattgg ggccagggca ccctggtgac cgtgagctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctggggga    720 ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                1353

<210> SEQ ID NO 5
<211> LENGTH: 214
```

```
<212> TYPE: PRT
<213> ORGANISM: Artificial Sequence
<220> FEATURE:
<223> OTHER INFORMATION: Synthetic Sequence

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 645
<212> TYPE: DNA
<213> ORGANISM: Artificial Sequence
<220> FEATURE:
<223> OTHER INFORMATION: Synthetic Sequence

<400> SEQUENCE: 6
gatattcaga tgacccagag cccgtcaagc ttaagcgcga gcgtgggcga tcgcgtgacc      60
attacctgcc gcgcgagcca ggatgtgaac accgcggtgg cgtggtatca gcagaaaccg     120
ggcaaagcgc cgaaactgct gatttatagc gcgagctttc tgtatagcgg cgtgccgagc     180
cgctttagcg gcagccgcag cggcaccgat tttaccctga ccattagcag cctgcagccg     240
gaagattttg cgacctatta ttgccagcag cattatacca ccccgccgac ctttggccag     300
ggtaccaaag tggaaattaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
```
ctgagctcgc ccgtcacaaa gagcttcaac aggggagagt gttag         645

<210> SEQ ID NO 7
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 7
caagctggct agcatggaat tggggctgag ctggg           35

<210> SEQ ID NO 8
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 8
atgggccctt ggtggaggct gagctcacgg                30

<210> SEQ ID NO 9
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 9
ccgtgagctc agcctccacc aagggcccat                30

<210> SEQ ID NO 10
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 10
aactttcttg tccacct           17

<210> SEQ ID NO 11
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 11
aggtggacaa gaaagtt           17

<210> SEQ ID NO 12
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 12
gcgtctagac tcgagtcatt tacccggaga cagggagagg c          41

<210> SEQ ID NO 13
<211> LENGTH: 31
<212> TYPE: DNA
<213> ORGANISM: Artificial Sequence

```
<220> FEATURE:
<223> OTHER INFORMATION: Synthetic Sequence

<400> SEQUENCE: 13
caagctggct agcatggaca tgagggtccc c                              31

<210> SEQ ID NO 14
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 14
gctcggcgcc gccacggtgc gttta                                     25

<210> SEQ ID NO 15
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 15
taaacgcacc gtggcggcgc cgagc                                     25

<210> SEQ ID NO 16
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 16
cgagctcgga tccttagcat tcgccgcggt t                              31

<210> SEQ ID NO 17
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 17
cgcgctagcg ccaccatgga attggggctg agc                            33

<210> SEQ ID NO 18
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 18
gcctgaaccg ccgcctcctg agctcacggt gaccggggta                     40

<210> SEQ ID NO 19
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 19
agtggtggag gaggttctga tattcagatg acccagagcc                     40
```

<210> SEQ ID NO 20
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 20
gggctctgcg gccgcacctc ttgtgatctg cagtttggta                    40

<210> SEQ ID NO 21
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 21
ggaggcggcg gttcaggcgg aggtggaagt ggtggaggag gttct              45

<210> SEQ ID NO 22
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 22
agaacctcct ccaccacttc cacctccgcc tgaaccgccg cctcc              45

<210> SEQ ID NO 23
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 23
ggtgcggccg cagagcccaa atcttgtgac aaaac                         35

<210> SEQ ID NO 24
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 24
gcgtctagac tcgagtcatt tacccggaga cagggagagg c                  41

<210> SEQ ID NO 25
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 25
cccccatccc ggaaggagct gaccaaga                                 28

<210> SEQ ID NO 26
<211> LENGTH: 28
<212> TYPE: DNA
<213> ORGANISM: Artificial Sequence
<220> FEATURE:
<223> OTHER INFORMATION: Synthetic Sequence

```
<400> SEQUENCE: 26
tcttggtcag ctccttccgg gatggggg                                          28

<210> SEQ ID NO 27
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 27
cccccatccc gggataggct gaccaagaac                                        30

<210> SEQ ID NO 28
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 28
gttcttggtc agcctatccc gggatggggg                                        30

<210> SEQ ID NO 29
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 29
accaggtcag cctgtggtgc ctggtcaaa                                         29

<210> SEQ ID NO 30
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 30
tttgaccagg caccacaggc tgacctggt                                         29

<210> SEQ ID NO 31
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 31
gtcagcctga cctgccgggt caaaggcttc tat                                    33

<210> SEQ ID NO 32
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 32
atagaagcct ttgacccggc aggtcaggct gac                                    33

<210> SEQ ID NO 33
```

<210> SEQ ID NO 33
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 33
gtcagcctga cctgcaaggt caaaggcttc tat        33

<210> SEQ ID NO 34
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 34
atagaagcct ttgaccttgc aggtcaggct gac        33

<210> SEQ ID NO 35
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 35
ctgacctgcc tggtcgatgg cttctatccc agc        33

<210> SEQ ID NO 36
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 36
gctgggatag aagccatcga ccaggcaggt cag        33

<210> SEQ ID NO 37
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 37
ggagaacaac tacgatacca cgcctcccgt        30

<210> SEQ ID NO 38
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 38
acgggaggcg tggtatcgta gttgttctcc        30

<210> SEQ ID NO 39
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 39
cgcctcccgt gctgaagtcc gacggctcct tc                                          32

<210> SEQ ID NO 40
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 40
gaaggagccg tcggacttca gcacgggagg cg                                          32

<210> SEQ ID NO 41
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 41
tccttcttcc tcgccagcaa gctcaccgt                                              29

<210> SEQ ID NO 42
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 42
acggtgagct tgctggcgag gaagaagga                                              29

<210> SEQ ID NO 43
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 43
tccttcttcc tcgtcagcaa gctcaccgt                                              29

<210> SEQ ID NO 44
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 44
acggtgagct tgctgacgag gaagaagga                                              29

<210> SEQ ID NO 45
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 45
cttcctctac agcgatctca ccgtggaca                                              29

<210> SEQ ID NO 46
<211> LENGTH: 29
<212> TYPE: DNA

<213> ORGANISM: Artificial Sequence
<220> FEATURE:
<223> OTHER INFORMATION: Synthetic Sequence

<400> SEQUENCE: 46
tgtccacggt gagatcgctg tagaggaag                           29

<210> SEQ ID NO 47
<211> LENGTH: 451
<212> TYPE: PRT
<213> ORGANISM: Artificial Sequence
<220> FEATURE:
<223> OTHER INFORMATION: Synthetic Sequence

<400> SEQUENCE: 47

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile

```
                    325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 48
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 48

Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Ser Val Ser Tyr Ile
                20                  25                  30
His Trp Phe Gln Gln Lys Pro Gly Ser Ser Pro Lys Pro Trp Ile Tyr
            35                  40                  45
Ala Thr Ser Asn Leu Ala Ser Gly Val Pro Val Arg Phe Ser Gly Ser
        50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Thr Ser Asn Pro Pro Thr
                85                  90                  95
Phe Gly Gly Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 49
<211> LENGTH: 444
<212> TYPE: PRT
<213> ORGANISM: Artificial Sequence
<220> FEATURE:
<223> OTHER INFORMATION: Synthetic Sequence

<400> SEQUENCE: 49

```
Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Ser Asp Phe
            20                  25                  30

Glu Met His Trp Val Lys Gln Thr Pro Val His Gly Leu Glu Trp Ile
        35                  40                  45

Gly Asp Ile Asp Pro Gly Thr Gly Asp Thr Ala Tyr Asn Leu Lys Phe
    50                  55                  60

Lys Gly Lys Ala Thr Leu Thr Thr Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Leu Gly Ala Phe Val Tyr Trp Gly Gln Gly Thr Leu Val Thr Val
            100                 105                 110

Ser Ala Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
```

```
                370                 375                 380
Glu Asn Asn Tyr Lys Thr Thr Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440
```

<210> SEQ ID NO 50
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 50

```
Asp Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
            20                  25                  30

Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 51
<211> LENGTH: 449
<212> TYPE: PRT
<213> ORGANISM: Artificial Sequence
<220> FEATURE:
<223> OTHER INFORMATION: Synthetic Sequence

<400> SEQUENCE: 51

```
Gln Val Gln Leu Lys Gln Ser Gly Pro Gly Leu Val Gln Pro Ser Gln
1               5                   10                  15
```

-continued

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly

```
<210> SEQ ID NO 52
<211> LENGTH: 214
<212> TYPE: PRT
<213> ORGANISM: Artificial Sequence
<220> FEATURE:
<223> OTHER INFORMATION: Synthetic Sequence

<400> SEQUENCE: 52

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

BISPECIFIC ANTIBODY

SEQUENCE LISTING

The instant application contains a Sequence Listing which has been submitted electronically in ASCII format and is hereby incorporated by reference in its entirety. Said ASCII copy, created on May 1, 2014, is named SEQ_103563-0162.txt and is 39.4 kilobytes in size.

BACKGROUND ART

Bispecific antibodies (BsAb) are antibodies or antibody-like molecules having two different binding specificities. BsAbs have broad applications in biomedicine, especially in immunotherapy for tumors. Presently, a focus of immunotherapy research is on how to utilize cell-mediated cytotoxicity of BsAb to kill tumor cells. A BsAb can be designed to target a tumor cell and an effector cell simultaneously, while triggering the effector cell's destruction of the tumor cell.

BsAb can be prepared by methods such as chemical engineering, cell engineering and genetic engineering. An advantage of genetic engineering is that the antibodies can be easily modified, which renders design and production of many different forms of bispecific antibody fragments, including diabodies, tanderm ScFv, and single-chain diabodies, as well as derivatives thereof (reviewed by Jin and Zhu, in "the design and engineering of IgG-Like bispecific antibodies", R E Kontermann (ed), Bispecific antibodies). Since those BsAbs do not have an IgG Fc domain, their small size enhances their penetration into tumors, but they have significantly shorter half-life in vivo and also lack the ADCC effect that is associated with the constant region of the antibody.

To improve the stability and therapeutic potential, recombinant genetic modifications were made in the heavy chains to facilitate their heterodimerization and to produce greater yields of Fc-containing IgG-like bispecific antibodies. Several rational design strategies have been used to engineer antibody CH3 chains for heterodimerizaiton, namely disulfide bonds, salt bridges, knobs-into-holes. The bases for creating knob and hole in the juxtaposed positions is that the knob and hole interaction will favor heterodimer formation, whereas the knob-knob and the hole-hole interaction will prevent homodimers formation due to the deletion of favorable interactions. While this knob-into-holes approach solves the heavy chain homodimerization problem, it did not address the issues regarding mispairing between the light chain and heavy chains from two different antibodies. Although it is possible to identify identical light chains for two different antibodies, the possibility of BsAb construction using two antibody sequences that can share the common light chain is very limited.

There is a need to provide better BsAbs that are easier to prepare, have better clinical stability and efficacy and/or reduced systematic toxicity.

DISCLOSURE OF INVENTION

Technical Problem

One embodiment of the present disclosure provides an antibody comprising (a) a light chain-heavy chain pair having specificity to a tumor cell or a microorganism; and (b) a fusion peptide comprising a single-chain variable fragment (scFv) and an Fc fragment comprising a CH2 domain and a CH3 domain, wherein the fusion peptide has specificity to an immune cell.

Solution to Problem

Technical Solution

In some aspects, the light chain-heavy chain pair has specificity to a tumor antigen. In one aspect, the tumor antigen is selected from the group consisting of EGFR, Her2, EpCAM, CD20, CD30, CD33, CD47, CD52, CD133, CEA, gpA33, Mucins, TAG-72, CIX, PSMA, folate-binding protein, GD2, GD3, GM2, VEGF, VEGFR, Integrin, a V b 3, a 5 b 1, ERBB2, ERBB3, MET, IGF1R, EPHA3, TRAILR1, TRAILR2, RANKL, FAP and Tenascin. In one aspect, the light chain-heavy chain pair has specificity to a protein that is overexpressed on a tumor cell as compared to a corresponding non-tumor cell.

In some aspects, the light chain-heavy chain pair has specificity to a virus or bacterium. In one aspect, the light chain-heavy chain pair has specificity to an endotoxin.

In some aspects, the immune cell is selected from the group consisting of a T cell, a B cell, a monocyte, a macrophage, a neutrophil, a dendritic cell, a phagocyte, a natural killer cell, an eosinophil, a basophil, and a mast cell.

In some aspects, the fusion peptide has specificity to an antigen selected from the group consisting of CD3, CD16, CD19, CD28 and CD64.

In some aspects, the light chain is bound to the heavy chain through a disulfide bond. In some aspects, the heavy chain is bound to the fusion peptide through one or more disulfide bonds. In one aspect, the heavy chain comprises a human or a humanized Fc fragment. In one aspect, the Fc fragment of the heavy chain comprises a human IgG Fc fragment. In one aspect, the Fc fragment of the fusion peptide comprises a human or a humanized Fc fragment. In one aspect, the Fc fragment of the fusion peptide comprises a human IgG Fc fragment.

In some aspects, the heavy chain and/or the Fc fragment of the fusion peptide comprise one or more substitutions, as compared to a wild-type antibody fragment, that form an ionic bond between the heavy chain and the Fc fragment. In one aspect, the substitutions are selected from Table 2.

In some aspects, the heavy chain and/or the Fc fragment of the fusion peptide comprises one or more substitutions, as compared to a wild-type antibody fragment, that form a knob-into-the-hole conformational pairing between the heavy chain and the Fc fragment. In one aspect, the substitutions are selected from Table 3.

In some aspects, the CH2 domain is located between the scFv fragment and the CH3 domain. In one aspect, the fusion peptide does not contain a CH1 domain.

Also provided, in one embodiment, is a composition comprising an antibody of any of the above embodiment. In one aspect, the carrier is a pharmaceutical carrier.

Another embodiment provides a complex comprising an antibody of any of the above embodiments bound to one or more antigens.

Further provided is a method of preparing an antibody comprising admixing (a) a light chain-heavy chain pair having specificity to an immune cell and (b) a fusion peptide comprising a single-chain variable fragment (scFv) and an Fc fragment comprising a CH2 domain and a CH3 domain, wherein the fusion peptide has specificity to a tumor cell. In one aspect, provided is an antibody obtainable by the method.

BRIEF DESCRIPTION OF DRAWINGS

Description of Drawings

Figure 1:
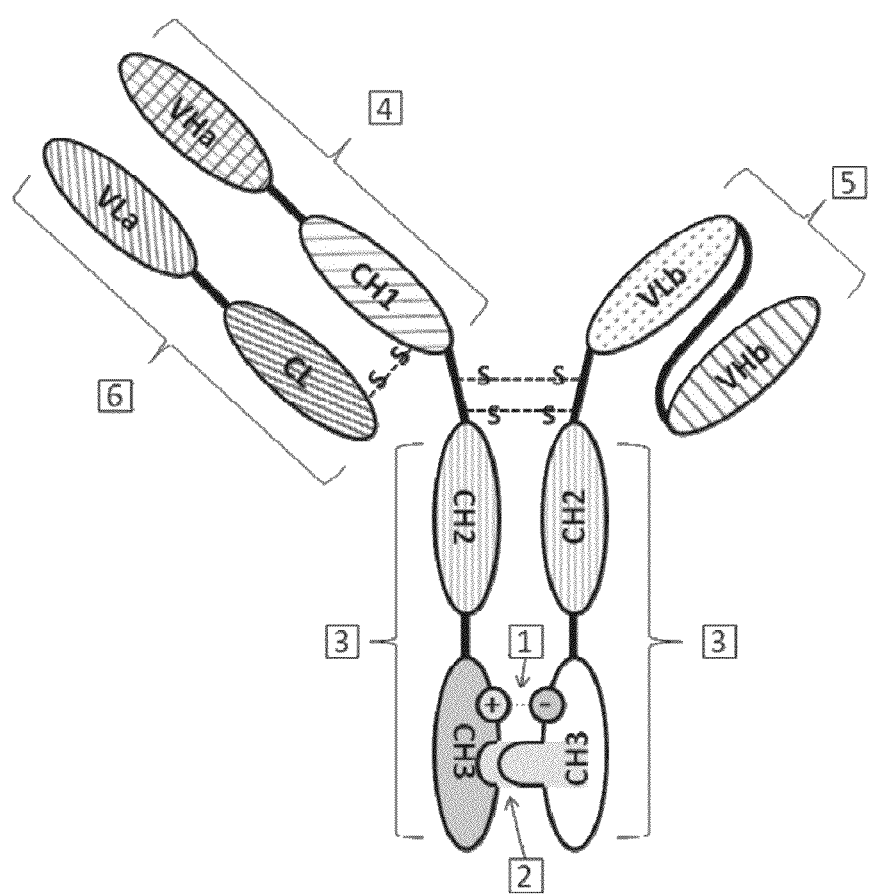

FIG. 1 illustrates the structure of one embodiment of the bispecific antibody of the present disclosure.

Figure 2:
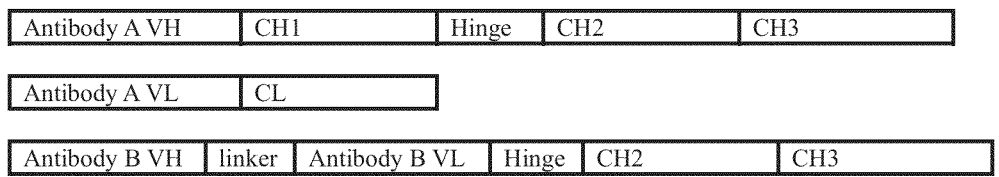

FIG. 2 shows the organization of expression vectors for each chain of the bispecific antibody of FIG. 1.

Figure 3:
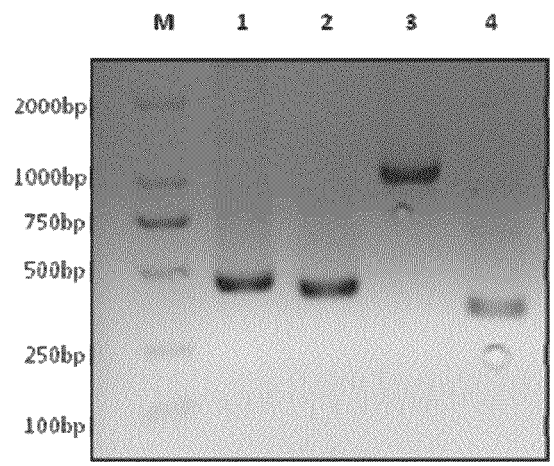

FIG. 3 is a 1% agarose gel electrophoresis photo: lane M: DL2000 marker; lane 1: Herceptin VH; lane 2: Herceptin VL; lane 3: human IgG1 CH region (CH1+Hinge+Fc); and lane 4: human Ig CL.

Figure 4:
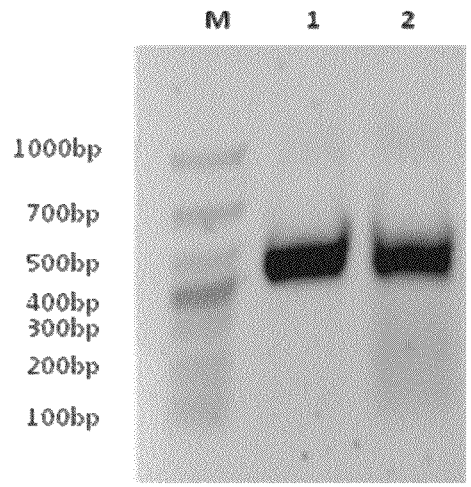

FIG. 4 is a 1% agarose gel electrophoresis photo: lane M: DL1000 DNA marker; lane 1: Humanized OKT3 (HOKT3) VH-linker; and lane 2: linker-HOKT3 VL.

Figure 5:
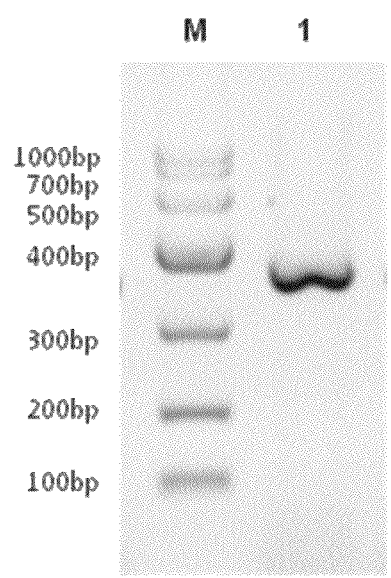

FIG. 5 is a 1% agarose gel electrophoresis photo: lane M: DL10000 DNA marker; and lane 1: HOKT3 single chain.

Figure 6:
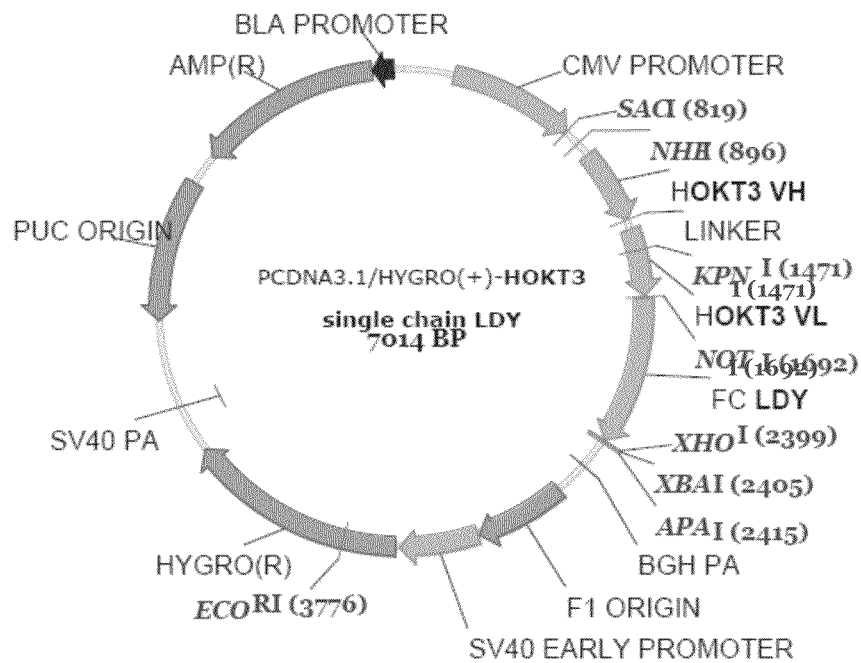
Figure 7:
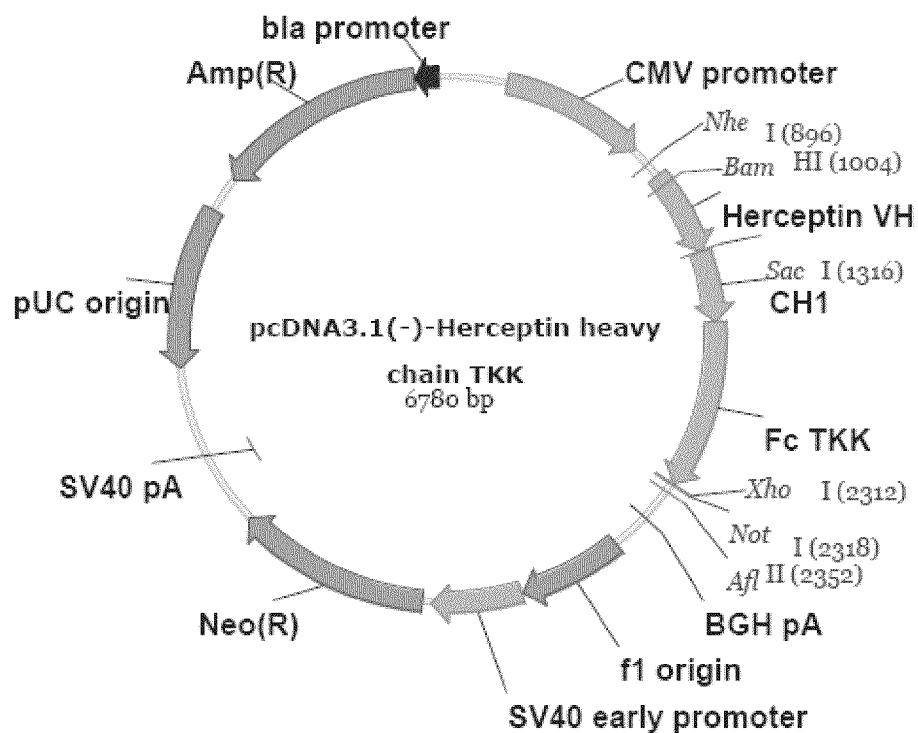
Figure 8:
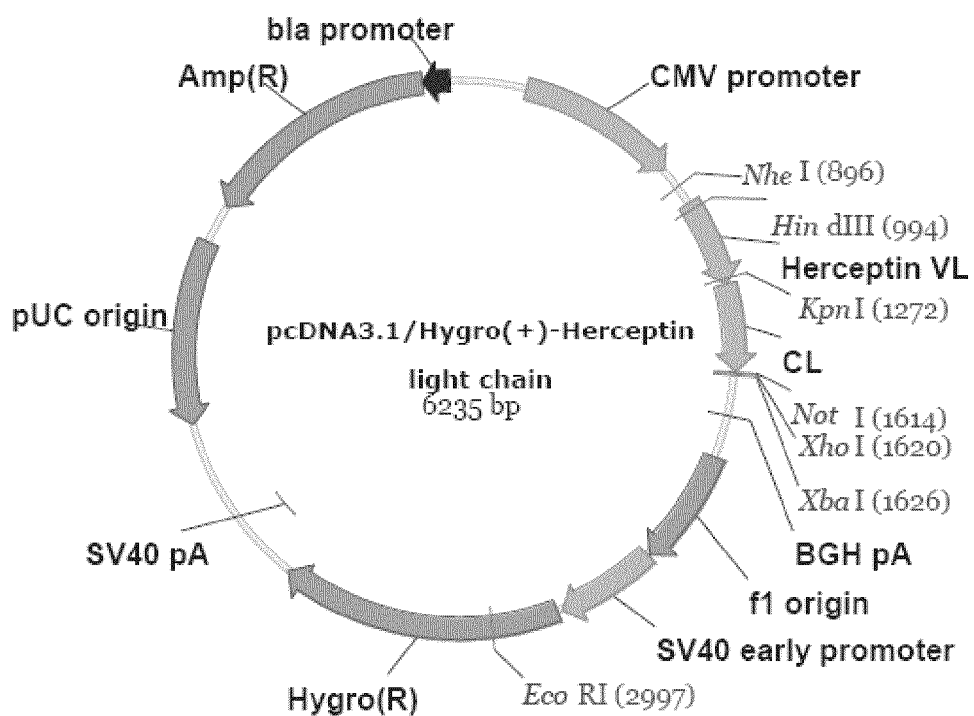

FIG. 6-8 are restriction maps of plasmids used for site-directed mutagenesis.

Figure 9:
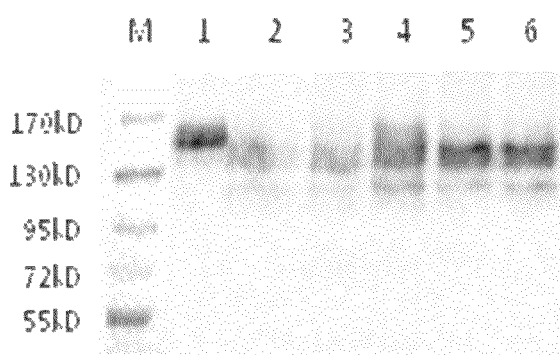

FIG. 9 shows a 6% gel SDS-PAGE and Western blot photo. Samples were 293F cells supernatant. Lane M: protein marker; lane 1: Herceptin mAb; lane 2: HOKT3 single-chain with T366W modifications+Herceptin heavy chain with Y407A modifications+Herceptin light chain; lane 3: HOKT3 single-chain with T366W K392D and K409D modifications (TKK)+Herceptin heavy chain with D356K D399K Y407A modifications (DDY)+Herceptin light chain; lane 4: HOKT3 single-chain with K392D and K409D modifications (KK)+Herceptin heavy chain with D356K D399K modifications (DD)+Herceptin light chain; lane 5: HOKT3 single-chain with T366W K392D and K409D modifications (TKK)+Herceptin heavy chain with L368R D399K Y407A modifications (LDY)+Herceptin light chain; and lane 6: HOKT3 single-chain with T366W K392D and K409D modifications (TKK)+Herceptin heavy chain with D399K Y407A modifications (DY)+Herceptin light chain.

Figure 10:
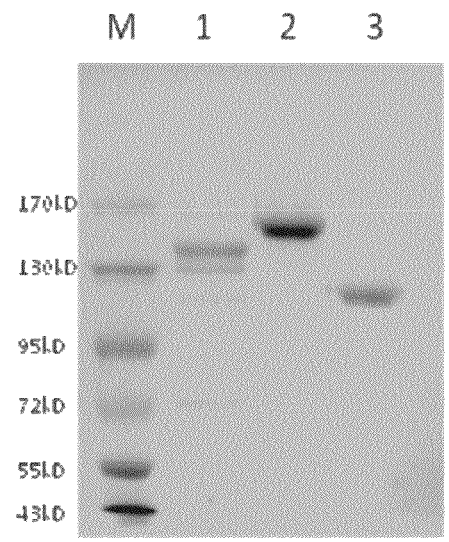

FIG. 10 shows a 6% SDS-PAGE gell with coomassie blue staining showing lane M: protein markers; and lane 1: purified MSBODY; lane 2: Herceptin; lane 3: HOKT3 Single chain.

FIG. 11 depicts a flow cytometry analysis of the cell surface binding of anti-Her2Xanti-CD3 MSBODY to BT474 cell (A) and peripheral blood mononeuclear cells (PBMC) (B) Gray line: PBS control; dark solid line: MSBODY; and dark dotted line: Herceptin.

Figure 12:
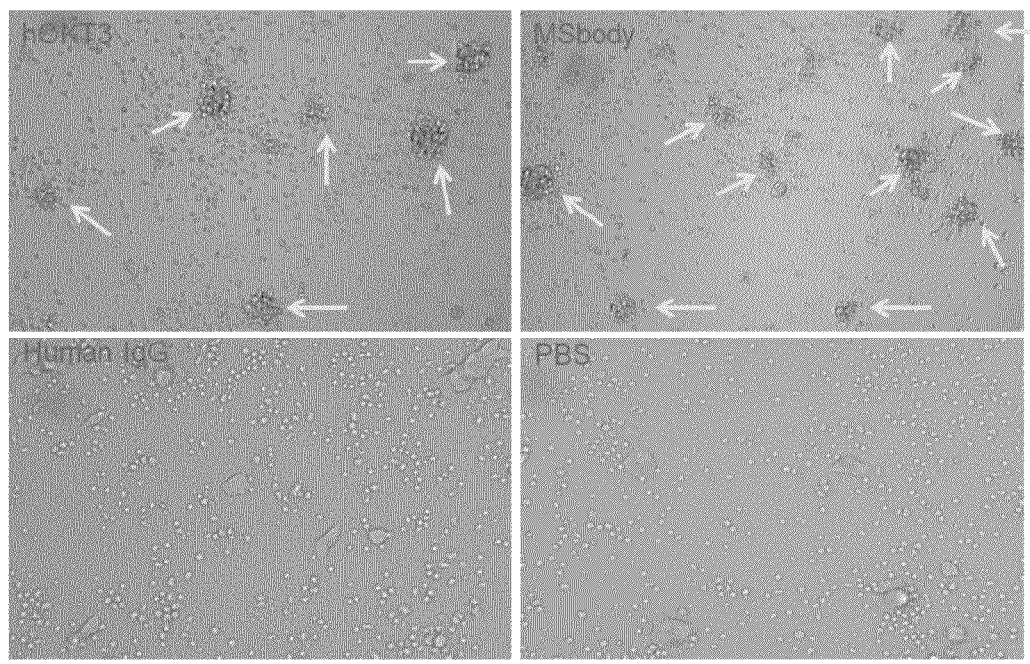

FIG. 12 includes four microscope images showing cell aggregation.

Figure 13:
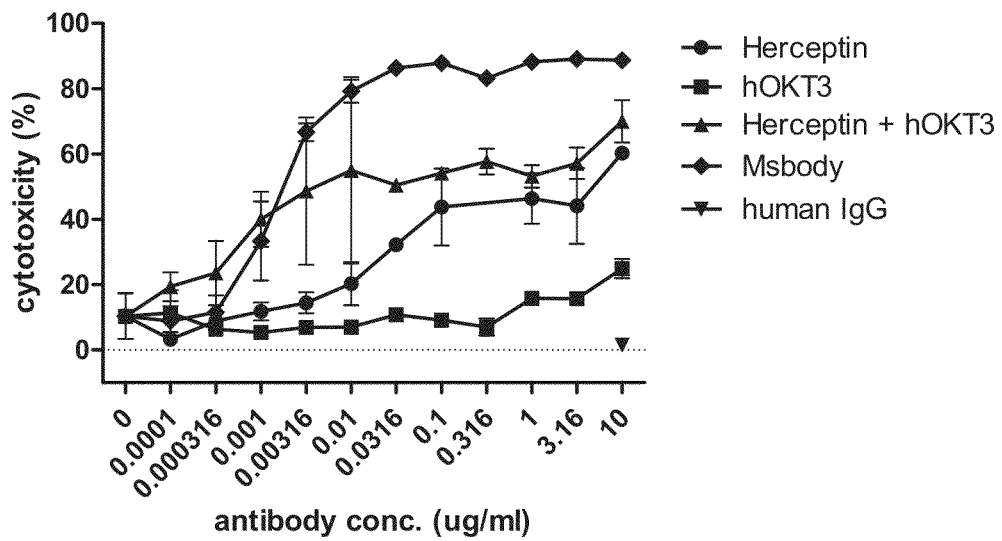

FIG. 13 shows antibody-induced cytotoxicity.

Figure 14:
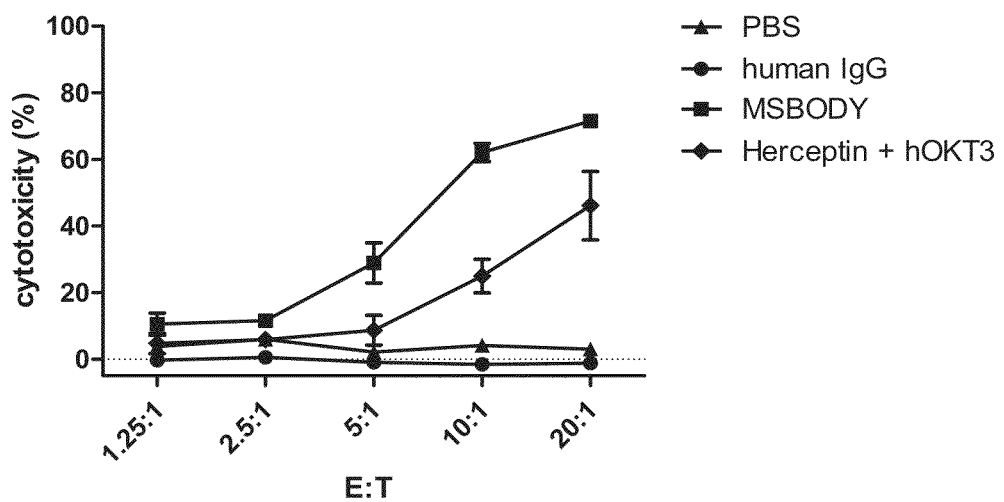

FIG. 14 shows antibody-induced cytotoxicity with PBS, human IgG, MSBODY, or the combination of Herceptin and hOKT3 (i.e., Herceptin+hOKT3).

FIG. 15A-E illustrate the structures of certain antibodies tested in Example 4. A: MSBODY; B: SMBODY; C: SSBODY; D: Herceptin single chain antibody; and E: HOKT3 single chain antibody.

FIG. 16A-B show the binding of anti-her2xanti-CD3 MSBODY and SMBODY, to BT474 cells (A) and PBMC cells (B).

Figure 17:
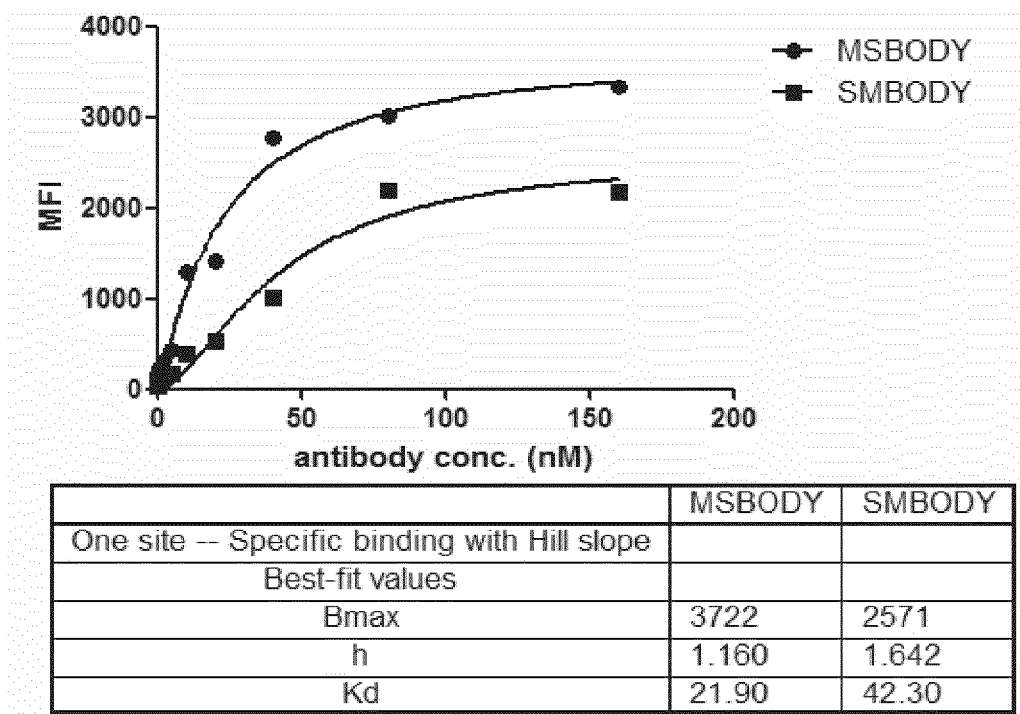

FIG. 17 shows that MSBODY has higher binding activity than SMBODY against BT474 cells.

Figure 18:
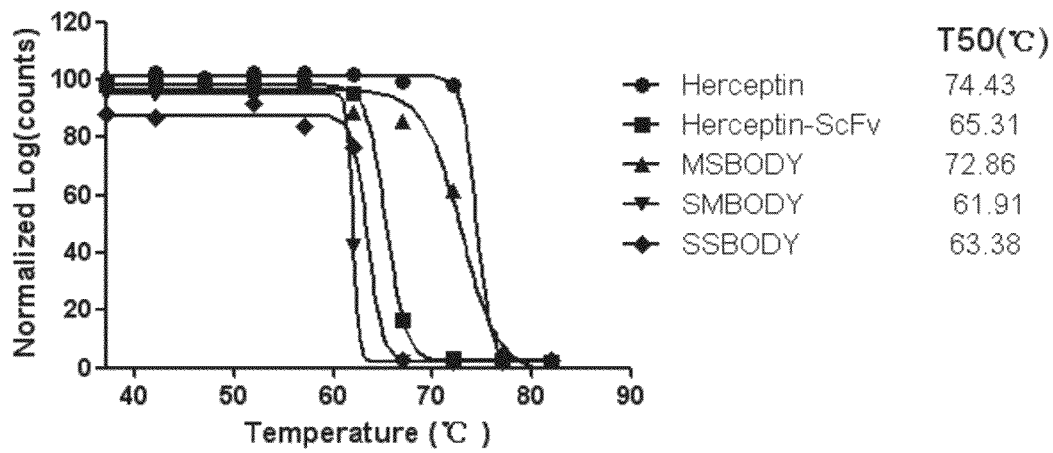

FIG. 18 shows the results of a thermal challenge assay

Figure 19:
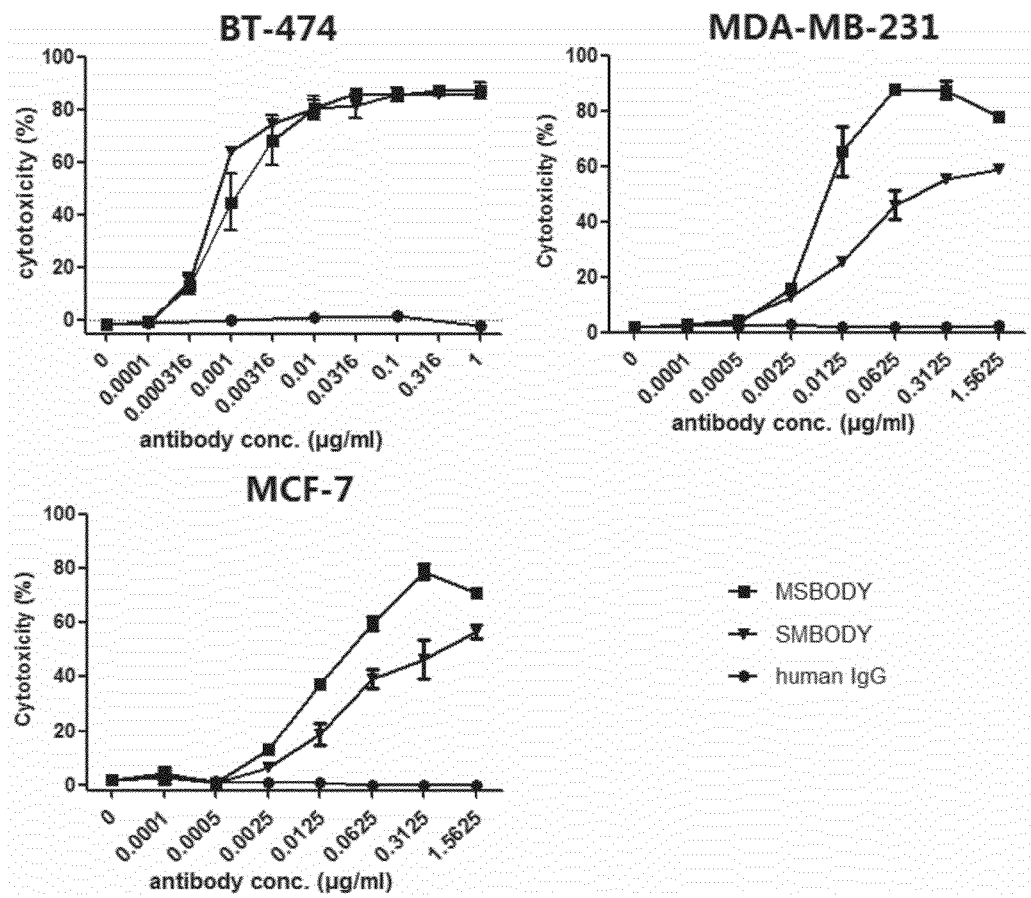

FIG. 19 shows the results of antibody induced cytotoxicity against BT474, MCF-7 and MDA-MB-231 cells.

FIG. 20 shows the numbering of amino acid residues of SEQ ID NO: 1 under the Kabat system. Amino acid position 216 marks the start of the hinge region; amino acid position 231 marks the start of the CH2 region, and amino acid position 341 marks the start of the CH3 region.

FIG. 21 shows the numbering of amino acid residues of SEQ ID NO: 3 under the Kabat system. Amino acid 118 marks the start of the CH1 region; amino acid position 216 marks the start of the hinge region; amino acid position 231 marks the start of the CH2 region, and amino acid position 341 marks the start of the CH3 region.

MODE FOR THE INVENTION

Mode for Invention

Definitions

It is to be noted that the term "a" or "an" entity refers to one or more of that entity; for example, "a bispecific antibody," is understood to represent one or more bispecific antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the NIH NCBI database. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the term "detectable label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma, \mu, \alpha, \delta, \epsilon \nu$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a b-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196: 901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

|  | Kabat | Chothia |
| --- | --- | --- |
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Bispecific Antibodies

One embodiment of the present disclosure provides a heterodimer antibody, which comprises of two different antigen-binding polypeptide units. In some aspects, the heterodimer differs in size from its corresponding homodimer, and the size difference can be utilized to facilitate separation of hetero- and homo-dimers.

In some aspects, one of the two antigen-binding polypeptide units comprises a light chain-heavy chain pair like a wild-type antibody. Throughout the disclosure, this unit is also referred to as a "monovalent unit." The other antigen-binding polypeptide unit, in some aspects, comprises a single chain variable fragment (scFv). Such an scFv can be fused to a constant fragment (Fc) of an antibody. This fusion peptide is also referred to as "single-chain unit" throughout the disclosure.

Surprisingly, the present disclosure demonstrates that such an asymmetric antibody is stable and retains high antigen-binding efficiency. This is unexpected because it has been demonstrated that even homodimers of single-chain antibodies are unstable under physiological conditions. Ahmad et al. "scFv Antibody: Principles and Clinical Application," *Clinical and Developmental Immunology*, 2012:980250 (2012), for instance, shows that scFv-based IgG like antibodies are not stable and need to be further engineered to reduce aggregates and improve stability.

Further, by virtue of the asymmetricity, a heterodimer has a different molecular weight from a homodimer comprising either one of the antigen-binding polypeptide units. Based on the molecular weight difference between the heterodimer and homodimer, the desired heterodimer can be readily separated from the homodimer.

The ability to easily separate heterodimers from homodimers is particular advantageous for the preparation of bispecific antibodies, in which each of the two antigen-binding polypeptides has specificity to a different epitope. This is because neither of the two types of homodimers (i.e., homodimer comprising the monovalent units, or the single-chain units) has the desired dual specificities provided by the heterodimer.

In one embodiment, such a bispecific antibody has specificity to a tumor cell or a microorganism and specificity to an immune cell, which brings the tumor cell or microorganism to close proximity of the immune cell, leading to the elimination of the tumor cell or microorganism through activated immune response.

In a particular aspect, the monovalent unit has specificity to a tumor cell or a microorganism, and the single-chain unit has specificity to an immune cell. The asymmetric bispecific antibody that has such arranged specificities is also referred to as a "monovalent single-chain bispecific antibody" or "MSBODY". By contrast, an asymmetric bispecific antibody, in which the monovalent unit has specificity to an immune cell and the single-chain unit has specificity to a tumor cell or a microorganism, is referred to as an "SMBODY". Another bispecific antibody has two single-chain units, of which one has specificity to a tumor cell or a microorganism and the other has specificity to an immune cell, is referred to as an "SSBODY".

An unexpected discovery of the present disclosure is that, even though MSBODY and SMBODY have the same binding motifs and similar molecular weight, when binding to the target tumor cell, however, MSBODY showed higher stability and affinity than SMBODY. In this context, it is interesting to note that although anti-Her2/anti-CD3 MSBODY and SMBODY resulted in similar cytotoxicity against high Her2-expressing BT474 cells, the MSBODY format showed higher cytotoxicity to low Her2-expressing breast cancer cell lines including MCF-7 and MDA-MB-231. As not all tumor cells that express a tumor antigen necessarily express the antigen at a high level, such a capability of MSBODY shows unique advantage in clinical applications.

In one embodiment, therefore, provided is an antibody comprising: (a) a light chain-heavy chain pair having specificity to a tumor cell; and (b) a fusion peptide comprising a single-chain variable fragment (scFv) and an Fc fragment comprising a CH2 domain and a CH3 domain, wherein the fusion peptide has specificity to an immune cell.

In another embodiment, provided is an antibody comprising: (a) a light chain-heavy chain pair having specificity to a microorganism, such as GP120 for HIV, HA2 for influenza, and shiga-like toxin 2B for *E. Coli*; and (b) a fusion peptide comprising a single-chain variable fragment (scFv) and an Fc fragment comprising a CH2 domain and a CH3 domain, wherein the fusion peptide has specificity to an immune cell.

FIG. 1 illustrates one embodiment of the bispecific antibody of the present disclosure. The left half (the monovalent unit) of the antibody is comprised of a light chain (6) and a heavy chain (3 and 4).

Also illustrated in FIG. 1, in one aspect, the light chain (6) includes a CL domain and a VL domain, VLa, targeting an epitope "a". Likewise, the heavy chain, in addition to the putative CH2 and CH3 domains, includes a CH1 domain and a VH domain, VHa, which also target epitope "a". In one aspect, the light chain and the heavy chain are bound to each other through a disulfide bond, e.g., between CL and CH1.

The single-chain unit is also illustrated in FIG. 1, containing a single-chain Fv (scFv) fragment (5) and a constant region (3) that includes CH2 and CH3. The scFv fragment is comprised of a VL (VLb) and a VH (VHb) domain each targeting an epitope "b" that is different from the epitope "a".

In some aspects, the heavy chain of the monovalent unit is bound to the fusion peptide through one or more disulfide bonds. In one aspect, the one or more disulfide bonds are formed between amino acid residues at the hinge regions between the CH1 (or VLb) and the CH2 domains.

In some aspects, the CH2 domain of the single-chain unit is located between the scFv fragment and the CH3 domain. In other words, the scFv fragment is connected at the CH2 end of the Fc fragment. In some aspects, the single-chain unit does not contain a CH1 domain.

In one aspect, either or both of the monovalent unit and the single-chain unit comprise human antibody sequences or humanized sequences. For instance, in one aspect, the heavy chain of the monovalent unit comprises a human or humanized Fc fragment. In a particular aspect, the Fc fragment of the heavy chain comprises a human IgG Fc fragment.

Likewise, in one aspect, the Fc fragment of the fusion peptide comprises a human or humanized Fc fragment. In a particular aspect the Fc fragment of the fusion peptide comprises a human IgG Fc fragment.

Modifications to the antibodies can be introduced to further stabilize or improve activity of the antibodies. For instance, in one aspect, the Fc fragment of the heavy chain of the monovalent unit and/or the Fc fragment of the fusion peptide can include one or more substitutions, as compared to a wild-type antibody fragment, that form an ionic bond between them.

In one aspect, one of the Fc fragments contains one or more substitutions with amino acid residues having a positive charge under physiological conditions and the other Fc fragment contains one or more substitutions with one or more amino acid residues having a negative charge under physiological conditions. In one aspect, the positively charged amino acid residue can be arginine (R), histidine (H) or lysine (K). In another aspect, the negatively charged amino acid residue can be aspartic acid (D) or glutamic acid (E). Amino acid residues that can be substituted include, without limitation, D356, E357, L368, K370, K392, D399 and K409. Table 2 below lists non-limiting examples of combinations of such substitutions.

TABLE 2

Combinations of amino acid substations leading to formation of an ionic bond between the monovalent unit and the single-chain unit

| Comb. No. | Substitution(s) on one Fc | Substitution(s) on the other Fc |
| --- | --- | --- |
| 1 | D356K D399K | K392D K409D |
| 2 | E357R L368R | K370D K409D |
| 3 | E357R L368K | K370D K409D |
| 4 | E357R D399K | K370D K409D |
| 5 | E357R | K370D |
| 6 | L368R D399K | K392D K409D |
| 7 | L368K D399K | K392D K409D |
| 8 | L368R D399K | K409D |
| 9 | L368K D399K | K409D |
| 10 | L368R | K409D |
| 11 | L368K | K409D |
| 12 | K370D K409D | E357R D399K |
| 13 | K370D K409D | E357R L368R |
| 14 | K370D K409D | E357R L368K |
| 15 | K370D K409D | E357R D399K |
| 16 | K370D K409D | E357R L368R |
| 17 | K370D K409D | E357R L368K |
| 18 | K370D | E357R |
| 19 | K370D | E357R |
| 20 | K392D K409D | D356K D399K |
| 21 | K392D K409D | L368R D399K |
| 22 | K392D K409D | L368K D399K |
| 23 | K392D K409D | D399K |
| 24 | D399K | K392D K409D |
| 25 | D399K | K409D |
| 26 | K409D | L368R |
| 27 | K409D | L368K |
| 28 | K409D | L368R D399K |
| 29 | K409D | L368K D399K |
| 30 | K409D | L368R |
| 31 | K409D | L368K |
| 32 | K409D | L368R D399K |
| 33 | K409D | L368K D399K |
| 34 | K409D | D399K |

In some aspects, the Fc fragment of the heavy chain of the monovalent unit and/or the Fc fragment of the fusion peptide can include one or more substitutions, as compared to a wild-type antibody fragment, that form a knob-into-the-hole conformational pairing between them. Knob-into-hole designs are known in the art. See, e.g., Ridgway et al. ""Knob-into-holes" engineering of antibody $C_H3$ domains for heavy chain heterodimerization," *Protein Engineering* 9(7):617-21 (1996).

In one aspect, K366 on one of the Fc fragment is substituted with a relatively large amino acid residue, such as tyrosine (Y) or tryptophan (W). Then Y407 on the other Fc fragment can be substituted with a relatively small amino acid residue, such as threonine (T), alanine (A) or valine (V). Table 3 below shows a few non-limiting examples of combinations of substitutions.

TABLE 3

Combinations of amino acid substations leading to formation of a knob-into-hole conformational pairing between the monovalent unit and the single-chain unit

| Comb. No. | Substitution(s) on one Fc | Substitution(s) on the other Fc |
|---|---|---|
| 1 | T366W | Y407A |
| 2 | T366W | Y407V |
| 3 | T366Y | Y407A |
| 4 | T366Y | Y407V |

In some aspects, the antibody can include either an ionic bond or a knob-into-hole or both of them. Table 4 below shows certain examples in this regard.

TABLE 4

Combinations of amino acid substations

| Comb. No. | Substitution(s) on one Fc | Substitution(s) on the other Fc |
|---|---|---|
| 1 | K370D | E357R |
| 2 | K409D | L368R |
| 3 | K409D | L368K |
| 4 | K409D | L368R D399K |
| 5 | K409D | L368K D399K |
| 6 | K370D K409D | E357R D399K |
| 7 | K370D K409D | E357R L368R |
| 8 | K370D K409D | E357R L368K |
| 9 | T366W K370D | E357R Y407A |
| 10 | T366W K370D | E357R Y407V |
| 11 | T366W K409D | L368R Y407A |
| 12 | T366W K409D | L368R Y407V |
| 13 | T366W K409D | L368K Y407A |
| 14 | T366W K409D | L368K Y407V |
| 15 | T366W K409D | L368R D399K Y407A |
| 16 | T366W K409D | L368R D399K Y407V |
| 17 | T366W K409D | L368K D399K Y407A |
| 18 | T366W K409D | L368K D399K Y407V |
| 19 | T366W K409D | D399K Y407A |
| 20 | T366W K409D | D399K Y407V |
| 21 | T366W K392D K409D | D399K Y407A |
| 22 | T366W K392D K409D | D399K Y407V |
| 23 | T366W K392D K409D | D356K D399K Y407A |
| 24 | T366W K392D K409D | D356K D399K Y407V |
| 25 | T366W K370D K409D | E357R D399K Y407A |
| 26 | T366W K370D K409D | E357R D399K Y407V |
| 27 | T366W K370D K409D | E357R L368R Y407A |
| 28 | T366W K370D K409D | E357R L368R Y407V |
| 29 | T366W K370D K409D | E357R L368K Y407A |
| 30 | T366W K370D K409D | E357R L368K Y407V |
| 31 | T366W K392D K409D | L368R D399K Y407A |
| 32 | T366W K392D K409D | L368R D399K Y407V |
| 33 | T366W K392D K409D | L368K D399K Y407A |
| 34 | T366W K392D K409D | L368K D399K Y407V |
| 35 | E357R T366W | K370D Y407A |
| 36 | E357R T366W | K370D Y407V |
| 37 | T366W L368R | Y407A K409D |
| 38 | T366W L368R | Y407V K409D |
| 39 | T366W L368K | Y407A K409D |
| 40 | T366W L368K | Y407V K409D |
| 41 | T366W L368R D399K | Y407A K409D |
| 42 | T366W L368R D399K | Y407V K409D |
| 43 | T366W L368K D399K | Y407A K409D |
| 44 | T366W L368K D399K | Y407V K409D |
| 45 | T366W D399K | Y407A K409D |
| 46 | T366W D399K | Y407V K409D |
| 47 | T366W D399K | K392D Y407A K409D |
| 48 | T366W D399K | K392D Y407V K409D |
| 49 | T366W D356K D399K | K392D Y407A K409D |
| 50 | T366W D356K D399K | K392D Y407V K409D |
| 51 | E357R T366W D399K | K370D Y407A K409D |
| 52 | E357R T366W D399K | K370D Y407V K409D |
| 53 | E357R T366W L368R | K370D Y407A K409D |
| 54 | E357R T366W L368R | K370D Y407V K409D |
| 55 | E357R T366W L368K | K370D Y407A K409D |
| 56 | E357R T366W L368K | K370D Y407V K409D |
| 57 | T366W L368R D399K | K392D Y407A K409D |
| 58 | T366W L368R D399K | K392D Y407V K409D |
| 59 | T366W L368K D399K | K392D Y407A K409D |
| 60 | T366W L368K D399K | K392D Y407V K409D |

In some aspects, the monovalent unit of the bispecific antibody of the present disclosure has specificity to a tumor cell. In one aspect, the monovalent unit specifically recognizes a tumor antigen.

A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CEA, gpA33, Mucins, TAG-72, CIX, PSMA, folate-binding protein, GD2, GD3, GM2, VEGF, VEGFR, Integrin, a V b 3, a 5 b 1, ERBB2, ERBB3, MET, IGF1R, EPHA3, TRAILR1, TRAILR2, RANKL, FAP and Tenascin.

In some aspects, the monovalent unit has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as Cystic Fibrosis.

In some aspects, the monovalent unit has specificity to an microorganism. Non-limiting examples of microorganism include microorganism surface receptors and endotoxins. Examples of endotoxins include, without limitation, lipopolysaccharide (LPS) and lipooligosaccharide (LOS).

In some aspects, the single-chain unit has specificity to an immune cell. In one aspect, the immune cell is selected from the group consisting of a T cell, a B cell, a monocyte, a macrophage, a neutrophil, a dendritic cell, a phagocyte, a natural killer cell, an eosinophil, a basophil, and a mast cell.

In one aspect, the single-chain unit specifically recognizes an antigen selected from the group consisting of CD3, CD16, CD19, CD28 and CD64.

Exemplary sequences for each of the polypeptide chains in the bispecific ligand are provided. In one aspect, the fusion peptide of the single-chain unit has an amino acid sequence of SEQ ID NO: 1. In one aspect, the heavy chain of the monovalent unit has an amino acid sequence of SEQ ID NO: 3. In one aspect, the light chain of the monovalent unit has an amino acid sequence of SEQ ID NO: 5.

Any of the antibodies or polypeptides described above may further include additional polypeptides, e.g., a signal peptide to direct secretion of the encoded polypeptide, antibody constant regions as described herein, or other heterologous polypeptides as described herein.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

In certain embodiments, an antigen-binding polypeptide comprises an amino acid sequence or one or more moieties not normally associated with an antibody. Exemplary modifications are described in more detail below. For example, a single-chain Fv antibody fragment of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In other embodiments, the antigen-binding polypeptides of the present disclosure may contain conservative amino acid substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE 5

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |

TABLE 5-continued

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies "84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Polynucleotides Encoding the Antibodies and Methods of Preparing the Antibodies

The present disclosure also provides for isolated polynucleotides or nucleic acid molecules encoding the antibodies, variants or derivatives thereof of the disclosure.

FIG. 2, for example, illustrates the organization of three polynucleotides encoding each of the peptides in the antibody as shown in FIG. 1.

Exemplary sequences encoding each of the polypeptide chains in the bispecific ligand are provided. In one aspect, the fusion peptide of the single-chain unit is encoded by a nucleic acid sequence of SEQ ID NO: 2. In one aspect, the heavy chain of the monovalent unit is encoded by a nucleic acid sequence of SEQ ID NO: 4. In one aspect, the light chain of the monovalent unit is encoded by a nucleic acid sequence of SEQ ID NO: 6.

The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci. USA* 57:6851-6855 (1984); Morrison et al., *Adv. Immunol.* 44:65-92 (1988); Verhoeyen et al., *Science* 239:1534-1536 (1988); Padlan, *Molec. Immun.* 25:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, *Science* 242:423-442 (1988); Huston et al., *Proc. Natl. Acad. Sci. USA* 55:5879-5883 (1988); and Ward et al., *Nature* 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in *E. coli* may also be used (Skerra et al., *Science* 242: 1038-1041 (1988)).

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska, et al., *Proc. Natl. Sci. USA* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 72:899-903 (1988). See also, U.S. Pat. No. 5,565,332, which is incorporated by reference in its entirety.)

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., *Proc. Natl. Acad. Sci. USA:* 851-855 (1984); Neuberger et al., *Nature* 372:604-608 (1984); Takeda et al., *Nature* 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Treatment and Diagnostic Methods

As described herein, the antigen-binding polypeptides, variants or derivatives of the present disclosure may be used in certain treatments and diagnostic methods associated with cancer or an infectious disease.

The present disclosure is further directed to antibody-based therapies which involve administering the bispecific antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat, inhibit or prevent diseases, disorders or conditions including malignant diseases, disorders, or conditions associated with such diseases or disorder such as diseases associated with increased cell survival, or the inhibition of apoptosis, for example cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. Antigen binding polypeptides, variants or derivatives thereof of the present disclosure are used to inhibit growth, progression, and/or metastasis of cancers, in particular those listed above or in the paragraph that follows.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

The antibodies of the present disclosure can also be used to treat an infectious disease caused by a microorganism, or kill a microorganism, by targeting the microorganism and an immune cell to effect elimination of the microorganism. In one aspect, the microorganism is a virus including RNA and DNA viruses, a Gram positive bacterium, a Gram negative bacterium, a protozoa or a fungus. Non-limiting examples of infectious diseases and related microorganisms are provided in Table 6 below.

TABLE 6

Infectious diseases and related microorganism sources.

| Infectious Disease | Microorganism Source |
|---|---|
| Acinetobacter infections | *Acinetobacter baumannii* |
| Actinomycosis | *Actinomyces israelii, Actinomyces gerencseriae* and *Propionibacterium propionicus* |
| African sleeping sickness (African trypanosomiasis) | *Trypanosoma brucei* |
| AIDS (Acquired immunodeficiency syndrome) | HIV (Human immunodeficiency virus) |
| Amebiasis | *Entamoeba histolytica* |
| Anaplasmosis | *Anaplasma* genus |
| Anthrax | *Bacillus anthracis* |
| Arcanobacterium haemolyticum infection | *Arcanobacterium haemolyticum* |
| Argentine hemorrhagic fever | Junin virus |
| Ascariasis | *Ascaris lumbricoides* |
| Aspergillosis | *Aspergillus* genus |
| Astrovirus infection | Astroviridae family |
| Babesiosis | *Babesia* genus |
| *Bacillus cereus* infection | *Bacillus cereus* |
| Bacterial pneumonia | multiple bacteria |
| Bacterial vaginosis (BV) | multiple bacteria |
| *Bacteroides* infection | *Bacteroides* genus |
| Balantidiasis | *Balantidium coli* |
| Baylisascaris infection | *Baylisascaris* genus |
| BK virus infection | BK virus |
| Black piedra | *Piedraia hortae* |
| *Blastocystis hominis* infection | *Blastocystis hominis* |
| Blastomycosis | *Blastomyces dermatitidis* |
| Bolivian hemorrhagic fever | Machupo virus |
| *Borrelia* infection | *Borrelia* genus |
| Botulism (and Infant botulism) | *Clostridium botulinum* |
| Brazilian hemorrhagic fever | Sabia |
| Brucellosis | *Brucella* genus |
| *Burkholderia* infection | usually *Burkholderia cepacia* and other *Burkholderia* species |
| Buruli ulcer | *Mycobacterium ulcerans* |
| Calicivirus infection (Norovirus and Sapovirus) | Caliciviridae family |
| Campylobacteriosis | *Campylobacter* genus |
| Candidiasis (Moniliasis; Thrush) | usually *Candida albicans* and other *Candida* species |
| Cat-scratch disease | *Bartonella henselae* |
| Cellulitis | usually Group A *Streptococcus* and *Staphylococcus* |
| Chagas Disease (American trypanosomiasis) | *Trypanosoma cruzi* |
| Chancroid | *Haemophilus ducreyi* |
| Chickenpox | Varicella zoster virus (VZV) |
| *Chlamydia* | *Chlamydia trachomatis* |
| *Chlamydophila pneumoniae* infection | *Chlamydophilapneumoniae* |
| Cholera | *Vibrio cholerae* |
| Chromoblastomycosis | usually Fonsecaea pedrosoi |

TABLE 6-continued

Infectious diseases and related microorganism sources.

| Infectious Disease | Microorganism Source |
|---|---|
| Clonorchiasis | *Clonorchis sinensis* |
| Clostridium difficile infection | *Clostridium difficile* |
| Coccidioidomycosis | *Coccidioides immitis* and *Coccidioides posadasii* |
| Colorado tick fever (CTF) | Colorado tick fever virus (CTFV) |
| Common cold (Acute viral rhinopharyngitis; Acute coryza) | usually rhinoviruses and coronaviruses. |
| Creutzfeldt-Jakob disease (CJD) | CJD prion |
| Crimean-Congo hemorrhagic fever (CCHF) | Crimean-Congo hemorrhagic fever virus |
| Cryptococcosis | *Cryptococcus neoformans* |
| Cryptosporidiosis | *Cryptosporidium* genus |
| Cutaneous larva migrans (CLM) | usually Ancylostoma braziliense; multiple other parasites |
| Cyclosporiasis | *Cyclospora cayetanensis* |
| Cysticercosis | *Taenia solium* |
| Cytomegalovirus infection | *Cytomegalovirus* |
| Dengue fever | Dengue viruses (DEN-1, DEN-2, DEN-3 and DEN-4) - Flaviviruses |
| Dientamoebiasis | *Dientamoeba fragilis* |
| Diphtheria | *Corynebacterium diphtheriae* |
| Diphyllobothriasis | *Diphyllobothrium* |
| Dracunculiasis | *Dracunculus medinensis* |
| Ebola hemorrhagic fever | Ebolavirus (EBOV) |
| Echinococcosis | *Echinococcus* genus |
| Ehrlichiosis | *Ehrlichia* genus |
| Enterobiasis (Pinworm infection) | *Enterobius vermicularis* |
| *Enterococcus* infection | *Enterococcus* genus |
| Enterovirus infection | *Enterovirus* genus |
| Epidemic typhus | *Rickettsia prowazekii* |
| Erythema infectiosum (Fifth disease) | Parvovirus B19 |
| Exanthem subitum (Sixth disease) | Human herpesvirus 6 (HHV-6) and Human herpesvirus 7 (HHV-7) |
| Fasciolopsiasis | *Fasciolopsis buski* |
| Fasciolosis | *Fasciola hepatica* and *Fasciola gigantica* |
| Fatal familial insomnia (FFI) | FFI prion |
| Filariasis | Filarioidea super family |
| Food poisoning by Clostridium perfringens | *Clostridium perfringens* |
| Free-living amebic infection | multiple |
| *Fusobacterium* infection | *Fusobacterium* genus |
| Gas gangrene (Clostridial myonecrosis) | usually *Clostridium perfringens*; other *Clostridium* species |
| Geotrichosis | *Geotrichum c andidum* |
| Gerstmann-Sträussler-Scheinker syndrome (GSS) | GSS prion |
| Giardiasis | *Giardia intestinalis* |
| Glanders | *Burkholderia mallei* |
| Gnathostomiasis | *Gnathostoma spinigerum* and *Gnathostoma hispidum* |
| Gonorrhea | *Neisseria gonorrhoeae* |
| Granuloma inguinale (Donovanosis) | *Klebsiella granulomatis* |
| Group A streptococcal infection | *Streptococcus pyogenes* |
| Group B streptococcal infection | *Streptococcus agalactiae* |
| Haemophilus influenzae infection | *Haemophilus influenzae* |
| Hand, foot and mouth disease (HFMD) | Enteroviruses, mainly Coxsackie A virus and Enterovirus 71 (EV71) |
| Hantavirus Pulmonary Syndrome (HPS) | Sin Nombre virus |
| Helicobacter pylori infection | *Helicobacter pylori* |
| Hemolytic-uremic syndrome (HUS) | *Escherichia coli* O157:H7, O111 and O104:H4 |
| Hemorrhagic fever with renal syndrome (HFRS) | Bunyaviridae family |
| Hepatitis A | Hepatitis A Virus |
| Hepatitis B | Hepatitis B Virus |
| Hepatitis C | Hepatitis C Virus |
| Hepatitis D | Hepatitis D Virus |
| Hepatitis E | Hepatitis E Virus |
| Herpes simplex | Herpes simplex virus 1 and 2 (HSV-1 and HSV-2) |
| Histoplasmosis | *Histoplasma capsulatum* |
| Hookworm infection | *Ancylostoma duodenale* and *Necator americanus* |
| Human bocavirus infection | Human bocavirus (HBoV) |
| Human ewingii ehrlichiosis | *Ehrlichia ewingii* |
| Human granulocytic anaplasmosis (HGA) | *Anaplasmaphagocytophilum* |

TABLE 6-continued

Infectious diseases and related microorganism sources.

| Infectious Disease | Microorganism Source |
| --- | --- |
| Human metapneumovirus infection | Human metapneumovirus (hMPV) |
| Human monocytic ehrlichiosis | *Ehrlichia chaffeensis* |
| Human papillomavirus (HPV) infection | Human papillomavirus (HPV) |
| Human parainfluenza virus infection | Human parainfluenza viruses (HPIV) |
| Hymenolepiasis | *Hymenolepis nana* and *Hymenolepis diminuta* |
| Epstein-Barr Virus Infectious Mononucleosis (Mono) | Epstein-Barr Virus (EBV) |
| Influenza (flu) | Orthomyxoviridae family |
| Isosporiasis | *Isospora belli* |
| Kawasaki disease | unknown; evidence supports that it is in-fectious |
| Keratitis | multiple |
| *Kingella kingae* infection | *Kingella kingae* |
| Kuru | Kuru prion |
| Lassa fever | Lassa virus |
| Legionellosis (Legionnaires' disease) | *Legionella pneumophila* |
| Legionellosis (Pontiac fever) | *Legionella pneumophila* |
| Leishmaniasis | *Leishmania* genus |
| Leprosy | *Mycobacterium leprae* and *Mycobacterium lepromatosis* |
| Leptospirosis | *Leptospira* genus |
| Listeriosis | *Listeria monocytogenes* |
| Lyme disease (Lyme borreliosis) | usually Borrelia burgdorferi and other *Borrelia* species |
| Lymphatic filariasis (Elephantiasis) | *Wuchereria bancrofti* and *Brugia malayi* |
| Lymphocytic choriomeningitis | *Lymphocytic choriomeningitis* virus (LCMV) |
| Malaria | *Plasmodium genus* |
| Marburg hemorrhagic fever (MHF) | Marburg virus |
| Measles | Measles virus |
| Melioidosis (Whitmore's disease) | *Burkholderia pseudomallei* |
| Meningitis | multiple |
| Meningococcal disease | *Neisseria meningitidis* |
| Metagonimiasis | usually *Metagonimus yokagawai* |
| Microsporidiosis | *Microsporidia phylum* |
| Molluscum contagiosum (MC) | Molluscum contagiosum virus (MCV) |
| Mumps | Mumps virus |
| Murine typhus (Endemic typhus) | *Rickettsia typhi* |
| *Mycoplasma pneumonia* | *Mycoplasma pneumoniae* |
| Mycetoma | numerous species of bacteria (Actinomycetoma) and fungi (Eumycetoma) |
| Myiasis | parasitic dipterous fly larvae |
| Neonatal conjunctivitis (Ophthalmia neonatorum) | most commonly Chlamydia trachomatis and *Neisseria gonorrhoeae* |
| (New) Variant Creutzfeldt-Jakob disease (vCJD, nvCJD) | vCJD prion |
| Nocardiosis | usually *Nocardia asteroides* and other *Nocardia* species |
| Onchocerciasis (River blindness) | *Onchocerca volvulus* |
| Paracoccidioidomycosis (South American blastomycosis) | *Paracoccidioides brasiliensis* |
| Paragonimiasis | usually Paragonimus westermani and other *Paragonimus* species |
| Pasteurellosis | *Pasteurella* genus |
| *Pediculosis capitis* (Head lice) | *Pediculus humanus capitis* |
| *Pediculosis corporis* (Body lice) | *Pediculus humanus corporis* |
| *Pediculosis pubis* (Pubic lice, Crab lice) | *Phthirus pubis* |
| Pelvic inflammatory disease (PID) | multiple |
| Pertussis (Whooping cough) | *Bordetella pertussis* |
| Plague | *Yersinia pestis* |
| Pneumococcal infection | *Streptococcus pneumoniae* |
| Pneumocystis pneumonia (PCP) | *Pneumocystis jirovecii* |
| Pneumonia | multiple |
| Poliomyelitis | Poliovirus |
| Prevotella infection | *Prevotella* genus |
| Primary amoebic meningoencephalitis (PAM) | usually *Naegleria fowleri* |
| Progressive multifocal leukoencephalopathy | JC virus |
| Psittacosis | *Chlamydophila psittaci* |
| Q fever | *Coxiella burnetii* |
| Rabies | Rabies virus |
| Rat-bite fever | *Streptobacillus moniliformis* and *Spirillum minus* |

TABLE 6-continued

Infectious diseases and related microorganism sources.

| Infectious Disease | Microorganism Source |
| --- | --- |
| Respiratory syncytial virus infection | Respiratory syncytial virus (RSV) |
| Rhinosporidiosis | *Rhinosporidium seeberi* |
| Rhinovirus infection | Rhinovirus |
| Rickettsial infection | *Rickettsia* genus |
| Rickettsialpox | *Rickettsia akari* |
| Rift Valley fever (RVF) | Rift Valley fever virus |
| Rocky mountain spotted fever (RMSF) | *Rickettsia rickettsii* |
| Rotavirus infection | Rotavirus |
| Rubella | Rubella virus |
| Salmonellosis | *Salmonella* genus |
| SARS (Severe Acute Respiratory Syndrome) | SARS coronavirus |
| Scabies | *Sarcoptes scabiei* |
| Schistosomiasis | *Schistosoma* genus |
| Sepsis | multiple |
| Shigellosis (Bacillary dysentery) | *Shigella* genus |
| Shingles (Herpes zoster) | Varicella zoster virus (VZV) |
| Smallpox (Variola) | Variola major or Variola minor |
| Sporotrichosis | *Sporothrix schenckii* |
| Staphylococcal food poisoning | *Staphylococcus* genus |
| Staphylococcal infection | *Staphylococcus* genus |
| Strongyloidiasis | *Strongyloides stercoralis* |
| Syphilis | *Treponema pallidum* |
| Taeniasis | *Taenia* genus |
| Tetanus (Lockjaw) | *Clostridium tetani* |
| Tinea barbae (Barber's itch) | usually *Trichophyton* genus |
| Tinea capitis (Ringworm of the Scalp) | usually *Trichophyton tonsurans* |
| Tinea corporis (Ringworm of the Body) | usually *Trichophyton* genus |
| Tinea cruris (Jock itch) | usually *Epidermophyton floccosum*, *Trichophyton rubrum*, and *Trichophyton mentagrophytes* |
| Tinea manuum (Ringworm of the Hand) | *Trichophyton rubrum* |
| Tinea nigra | usually *Hortaea werneckii* |
| Tinea pedis (Athlete's foot) | usually *Trichophyton* genus |
| Tinea unguium (Onychomycosis) | usually *Trichophyton* genus |
| Tinea versicolor (Pityriasis versicolor) | *Malassezia* genus |
| Toxocariasis (Ocular Larva Migrans (OLM)) | *Toxocara canis* or *Toxocara cati* |
| Toxocariasis (Visceral Larva Migrans (VLM)) | *Toxocara canis* or *Toxocara cati* |
| Toxoplasmosis | *Toxoplasma gondii* |
| Trichinellosis | *Trichinella spiralis* |
| Trichomoniasis | *Trichomonas vaginalis* |
| Trichuriasis (Whipworm infection) | *Trichuris trichiura* |
| Tuberculosis | usually *Mycobacterium tuberculosis* |
| Tularemia | *Francisella tularensis* |
| Ureaplasma urealyticum infection | *Ureaplasma urealyticum* |
| Venezuelan equine encephalitis | Venezuelan equine encephalitis virus |
| Venezuelan hemorrhagic fever | Guanarito virus |
| Viral pneumonia | multiple viruses |
| West Nile Fever | West Nile virus |
| White piedra (Tinea blanca) | *Trichosporon beigelii* |
| *Yersinia pseudotuberculosis* infection | *Yersinia pseudotuberculosis* |
| Yersiniosis | *Yersinia enterocolitica* |
| Yellow fever | Yellow fever virus |
| Zygomycosis | Mucorales order (Mucormycosis) and Entomophthorales order (Entomophthoramycosis) |

A specific dosage and treatment regimen for any particular patient will depend upon a variety of factors, including the particular antigen-binding polypeptide, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antigen-binding polypeptides, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intraarticular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In another embodiment, the antigen-binding polypeptide or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the antigen-binding polypeptide or composition can be delivered in a controlled release system. In one embodiment, a pump may be used (see Sefton, 1987, CRC Crit. Ref Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

In a specific embodiment where the composition of the disclosure comprises a nucleic acid or polynucleotide encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc.

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-a.

In additional embodiments, the compositions of the disclosure are administered in combination with other therapeutic or prophylactic regimens, such as, for example, radiation therapy.

Compositions

The present disclosure also provides pharmaceutical compositions. Such compositions comprise an effective amount of an antibody, and an acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1

Preparation of an Anti-Her2/Neu-Anti-CD3 Bispecific Antibody

Materials

Polynucleotides encoding VL and VH of anti human Her2 humanized monoclonal antibody Herceptin, VL and VH of anti human CD3 humanized monoclonal antibody HOKT3, IgG1 heavy chain constant region CH1, the hinge region of Hinge and Fc, and kappa chain constant region of CL were obtained from Life Technologies Inc. (Carlsbad, Calif.). The linker sequence, (GGGGS)$_3$ (residues 120 to 134 of SEQ ID NO: 1), connecting the OKT3 ScFv and VL and VH, was synthesized using conventional methods.

Methods and Results

1. Construction of Expression Vectors pcDNA3.1 (−) was used as the expression vector to prepare the Herceptin heavy chain expression construct. pcDNA3.1 (+) Hygro was used as expression vector to prepare the Herceptin light chain expression construct and the HOKT3 single-chain construct. Primers were designed according to the sequences of VL, VH, ScFv, CH1 and Fc and multiple cloning sites of pcDNA3.1 (−) and pcDNA3.1 (+) Hygro vectors (Table 7). The VL and CL, VH and CH1, CH1 and Fc, ScFv VL and VH, ScFv and Fc fragments were connected by the overlap extension PCR method.

TABLE 7

PCR primer sequences

| RE | Sequence | SEQ ID NO. |
|---|---|---|
| HerVH-F (NheI) | CAAGCTGGCTAGCATGGAATTGGGGCTGAGCTGGG | 7 |
| HerVH-R | ATGGGCCCTTGGTGGAGGCTGAGCTCACGG | 8 |
| CH1-F | CCGTGAGCTCAGCCTCCACCAAGGGCCCAT | 9 |
| CH1-R | AACTTTCTTGTCCACCT | 10 |
| Fc-F | AGGTGGACAAGAAAGTT | 11 |
| Fc-R (XhoI) | GCGTCTAGACTCGAGTCATTTACCCGGAGACAGGGAGAGGC | 12 |
| HerVL-F (NheI) | CAAGCTGGCTAGCATGGACATGAGGGTCCCC | 13 |
| HerVL-R | GCTCGGCGCCGCCACGGTGCGTTTA | 14 |
| HerCL-F | TAAACGCACCGTGGCGGCGCCGAGC | 15 |
| HerCL-R (BamHI) | CGAGCTCGGATCCTTAGCATTCGCCGCGGTT | 16 |
| H OKT3VH-F (NheI) | CGCGCTAGCGCCACCATGGAATTGGGGCTGAGC | 17 |
| HOKT3VH-R | GCCTGAACCGCCGCCTCCTGAGCTCACGGTGACCGGGGTA | 18 |
| HOKT3VL-F | AGTGGTGGAGGAGGTTCTGatattcagatgacccagagcc | 19 |
| HOKT3VL-R (NotI) | GGGCTCTGCGGCCGCACCTCTTGTGATCTGCAGTTTGGTA | 20 |
| Linker-F | GGAGGCGGCGGTTCAGGCGGAGGTGGAAGTGGTGGAGGAGGTTCT | 21 |

TABLE 7-continued

PCR primer sequences

| RE | Sequence | SEQ ID NO. |
|---|---|---|
| Linker-R | AGAACCTCCTCCACCACTTCCACCTCCGCCTGAACCGCCGCCTCC | 22 |
| ScFvFc-F (Not) | GGTGCGGCCGCAGAGCCCAAATCTTGTGACAAAAC | 23 |
| ScFvFc-R (XbaI) | GCGTCTAGACTCGAGTCATTTACCCGGAGACAGGGAGAGGC | 24 |

PCR amplification conditions for VL, CL, VH and CH1 included incubation at 95° C. for 5 minutes followed by 25 cycles of 30 seconds of degeneration at 95° C., 30 seconds annealing at 56° C., 1 minute extension at 72° C., with a closing extension for 10 minutes at 72° C. FIG. 3 presents a gel picture showing the PCR products.

PCR amplification conditions for Fc and ScFv were similar except that each of the 25 cycles included 1 minute of degeneration at 95° C., 1 minute annealing at 56° C., and 2 minutes extension at 72° C. 1 minute. FIG. 4 presents a gel picture showing the PCR products.

Overlap extension PCT was used to connect VH and CH1, and VL and CL of Herceptin. Equal amounts of recovered VH and CH1, or VL and CL, and CH1 and Fc served as templates and primers to each other. Other conditions are similar to conventional PCR, with 2 cycles of: 2 minutes of denaturing at 95° C., 2 minutes of annealing at 55° C., 2 minutes of extension at 72° C. Then VH 5'end oligonucleotide primers and CL 3' end primers were added, incubated with 25 cycles of 95° C. denaturing for 1 minute, 1 minute at 56° C. for annealing, and extension for 2 minutes at 72° C. The closing loop included 10 minutes extension at 72° C.

The conditions of overlap extension PCR connection for VH-CH1 and Fc, ScFv and Fc included recovered VHCH1 with equal amount of Fc, ScFv and Fc as template and primer. The initial incubation included 2 cycles of 95° C. denaturing for 2 minutes, 55° C. annealing for 2 minutes, and extension at 72° C. for 3 minutes. VH 5'end oligonucleotide primers and CL 3' end primer were then added, followed by 25 cycles of 1 minute denaturing at 95° C., 1 minute annealing at 56° C., and 3 minutes extension at 72° C. The closing a loop included 10 minutes extension at 72° C. FIG. 5 presents a gel picture showing the PCR products.

PCR products were collected with a DNA fragment Recovery Kit and the VH-CH1-Fc fragment was isolated with dual digestions with NheI and XhoI. The fragment was then inserted into the pcDNA3.1(−) vector and was named pcDNA3.1(−)-Herceptin Heavy Chain. Likewise, the ScFv-Fc fragment for HOKT3 (with dual digestion by NheI and XhoI), the VL-CL fragment of Herceptin (with dual digestion by NheI and BamHI), were also inserted into pcDNA3.1(+) Hygro vector and were named pcDNA3.1(+)Hygro-HOKT3 single chain and pcDNA3.1(+)Hygro-Herceptin light chain, respectively.

2. Point Mutations

Point mutations were generated with Quickchange® Site-Directed Mutagenesis Kit and primers (Table 8) for pcDNA3.1(−)-Herceptin Heavy chain and pcDNA3.1 (+) Hygro-HOKT3 single chain Fc. The reactions were carried out in accordance with kit manuals. The mutations were confirmed by sequencing (sequencing vectors are shown in FIG. 6-8).

TABLE 8

Site-directed mutagenesis primers sequence

| Primer | Sequence | SEQ ID NO. |
|---|---|---|
| D356K-F | CCCCCATCCCGGAAGG AGCTGACCAAGA | 25 |
| D356K-R | TCTTGGTCAGCTCCTTC CGGGATGGGGG | 26 |
| E357R-F | CCCCCATCCCGGGATA GGCTGACCAAGAAC | 27 |
| E357R-R | GTTCTTGGTCAGCCTAT CCCGGGATGGGGG | 28 |
| T366W-F | ACCAGGTCAGCCTGTG GTGCCTGGTCAAA | 29 |
| T366W-R | TTTGACCAGGCACCAC AGGCTGACCTGGT | 30 |
| L368R-F | GTCAGCCTGACCTGCC GGGTCAAAGGCTTCTA T | 31 |
| L368R-R | ATAGAAGCCTTTGACC CGGCAGGTCAGGCTGA C | 32 |
| L368K-F | GTCAGCCTGACCTGCA AGGTCAAAGGCTTCTA T | 33 |
| L368K-R | ATAGAAGCCTTTGACC TTGCAGGTCAGGCTGA C | 34 |
| K370D-F | CTGACCTGCCTGGTCG ATGGCTTCTATCCCAG C | 35 |
| K370D-R | GCTGGGATAGAAGCCA TCGACCAGGCAGGTCA G | 36 |
| K392D-F | GGAGAACAACTACGAT ACCACGCCTCCCGT | 37 |
| K392D-R | ACGGGAGGCGTGGTAT CGTAGTTGTTCTCC | 38 |
| D399K-F | CGCCTCCCGTGCTGAA GTCCGACGGCTCCTTC | 39 |
| D399K-R | GAAGGAGCCGTCGGAC TTCAGCACGGGAGGCG | 40 |
| Y407A-F | TCCTTCTTCCTCGCCAG CAAGCTCACCGT | 41 |
| Y407A-R | ACGGTGAGCTTGCTGG CGAGGAAGAAGGA | 42 |
| Y407V-F | TCCTTCTTCCTCGTCAG CAAGCTCACCGT | 43 |
| Y407V-R | ACGGTGAGCTTGCTGA CGAGGAAGAAGGA | 44 |
| K409D-F | CTTCCTCTACAGCGAT CTCACCGTGGACA | 45 |
| K409D-R | TGTCCACGGTGAGATC GCTGTAGAGGAAG | 46 |

Table 9 below shows the sequences of each of the chains in the anti-Her2/neu-anti-CD3 bispecific antibody.

TABLE 9

Polypeptide and nucleic acid sequences of the bispecific antibody

Single-chain fusion peptide
(SEQ ID NO: 1)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSGGGGSGGGGSGGGGSQIVLTQSPAIMSASPG

EKVTMTCSASSSVSYMNWYQQKSGTSPKRWIYDTSKLASGVPAHFRGSGS

GTSYSLTISGMEAEDAATYYCQQWSSNPFTEGSGTKLEINRGAAAEPKSC

DKTHTCPPCPAPELLGGPSVFLEPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFELYSKLTVDKSRWQQG

NVFSCSVMHEALHNHYTQKSLSLSPGK

Single-chain fusion peptide, nucleic acid
(SEQ ID NO: 2)
CAGGTGCAGCTGGTGCAGAGCGGCGGCGGCGTCGTGCAGCCGGGCAGGTC

CCTGAGACTGTCTTGTAAGGCTTCTGGATACACCTTCACTAGATACACAA

TGCACTGGGTCAGACAGGCTCCTGGAAAGGGACTCGAGTGGATTGGATAC

TABLE 9-continued

Polypeptide and nucleic acid sequences of the bispecific antibody

ATTAATCCTAGCAGAGGTTATACTAACTACAATCAGAAGTTTAAGGACAG

ATTCACAATTTCTACTGACAAATCTAAGAGTACAGCCTTCCTGCAGATGG

ACTCACTCAGACCTGAGGATACCGGAGTCTATTTTTGTGCTAGATATTAC

GATGACCACTACTGTCTGGACTACTGGGGCCAAGGTACCCCGGTCACCGT

GAGCTCAGGAGGCGGCGGTTCAGGCGGAGGTGGAAGTGGTGGAGGAGGT

T

CTGATATTCAGATGACCCAGAGCCCGTCAAGCTTATCTGCTTCTGTCGGA

GACAGAGTCACAATCACATGTTCTGCTTCTAGCTCTGTCTCTTACATGAA

CTGGTATCAGCAGACACCTGGAAAGGCTCCTAAGCGGTGGATCTACGACA

CATCTAAGCTCGCTTCTGGAGTCCCTTCTAGATTCTCTGGTTCTGGCTCT

GGAACAGACTACACATTCACAATCTCTTCTCTCCAACCTGAGGACATCGC

TACATACTACTGCCAACAGTGGTCTAGCAATCCTTTCACATTCGGACAGG

GTACCAAACTGCAGATCACAAGAGGTGCGGCCGCAGAGCCCAAATCTTGT

GACAAAACTCACACATGCCCACCGTGCCCAGCACCTGAACTCCTGGGGGG

ACCGTCAGTCTTCCTCTTCCCCCCAAAACCCAAGGACACCCTCATGATCT

CCCGGACCCCTGAGGTCACATGCGTGGTGGTGGACGTGAGCCACGAAGAC

CCTGAGGTCAAGTTCAACTGGTACGTGGACGGCGTGGAGGTGCATAATGC

CAAGACAAAGCCGCGGGAGGAGCAGTACAACAGCACGTACCGTGTGGTC

A

GCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTC

CAAAGCCAAAGGGCAGCCCCGAGAACCACAGGTGTACACCCTGCCCCCAT

CCCGGGATGAGCTGACCAAGAACCAGGTCAGCCTGACCTGCCTGGTCAAA

GGCTTCTATCCCAGCGACATCGCCGTGGAGTGGGAGAGCAATGGGCAGCC

GGAGAACAACTACAAGACCACGCCTCCCGTGCTGGACTCCGACGGCTCCT

TCTTCCTCTACAGCAAGCTCACCGTGGACAAGAGCAGGTGGCAGCAGGGG

AACGTCTTCTCATGCTCCGTGATGCATGAGGCTCTGCACAACCACTACAC

GCAGAAGAGCCTCTCCCTGTCTCCGGGTAAATGA

Heavy chain of the monovalent unit (SEQ ID NO: 3)

EVQLVESGGGLVQPGGSLRLSCAASGENIKDTYIHWVRQAPGKGLEWVAR

IYPTNGYTRYADSVKGRETISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

TABLE 9-continued

Polypeptide and nucleic acid sequences of the bispecific antibody

Heavy chain of the monovalent unit, nucleic acid
(SEQ ID NO: 4)

GAAGTGCAGCTGGTGGAAAGCGGCGGCGGCCTGGTGCAGCCGGGCGGAT C

CCTGCGCCTGAGCTGCGCGGCGAGCGGCTTTAACATTAAAGATACCTATA

TTCATTGGGTGCGCCAGGCGCCGGGCAAAGGCCTGGAATGGGTGGCGCGC

ATTTATCCGACCAACGGCTATACCCGCTATGCGGATAGCGTGAAAGGCCG

CTTTACCATTAGCGCGGATACCAGCAAAAACACCGCGTATCTGCAGATGA

ACAGCCTGCGCGCGGAAGATACCGCGGTGTATTATTGCAGCCGCTGGGGC

GGCGATGGCTTTTATGCGATGGATTATTGGGGCCAGGGCACCCTGGTGAC

CGTGAGCTCAGCCTCCACCAAGGGCCCATCGGTCTTCCCCCTGGCACCCT

CCTCCAAGAGCACCTCTGGGGGCACAGCGGCCCTGGGCTGCCTGGTCAAG

GACTACTTCCCCGAACCGGTGACGGTGTCGTGGAACTCAGGCGCCCTGAC

CAGCGGCGTGCACACCTTCCCGGCTGTCCTACAGTCCTCAGGACTCTACT

CCCTCAGCAGCGTGGTGACCGTGCCCTCCAGCAGCTTGGGCACCCAGACC

TACATCTGCAACGTGAATCACAAGCCCAGCAACACCAAGGTGGACAAGAA

AGTTGAGCCCAAATCTTGTGACAAAACTCACACATGCCCACCGTGCCCAG

CACCTGAACTCCTGGGGGGACCGTCAGTCTTCCTCTTCCCCCCAAAACCC

AAGGACACCCTCATGATCTCCCGGACCCCTGAGGTCACATGCGTGGTGGT

GGACGTGAGCCACGAAGACCCTGAGGTCAAGTTCAACTGGTACGTGGACG

GCGTGGAGGTGCATAATGCCAAGACAAAGCCGCGGGAGGAGCAGTACAA

C AGCACGTACCGTGTGGTCAGCGTCCTCACCGTCCTGCACCAGGACTGGCT

GAATGGCAAGGAGTACAAGTGCAAGGTCTCCAACAAAGCCCTCCCAGCCC

CCATCGAGAAAACCATCTCCAAAGCCAAAGGGCAGCCCCGAGAACCACA

G

GTGTACACCCTGCCCCCATCCCGGGATGAGCTGACCAAGAACCAGGTCAG

CCTGACCTGCCTGGTCAAAGGCTTCTATCCCAGCGACATCGCCGTGGAGT

GGGAGAGCAATGGGCAGCCGGAGAACAACTACAAGACCACGCCTCCCGT

G CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

TGA

Light chain of the monovalent unit
(SEQ ID NO: 5)

DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Light chain of the monovalent unit, nucleic acid
(SEQ ID NO: 6)

GATATTCAGATGACCCAGAGCCCGTCAAGCTTAAGCGCGAGCGTGGGCGA

TCGCGTGACCATTACCTGCCGCGCGAGCCAGGATGTGAACACCGCGGTGG

TABLE 9-continued

Polypeptide and nucleic acid sequences of the bispecific antibody

```
CGTGGTATCAGCAGAAACCGGGCAAAGCGCCGAAACTGCTGATTTATAGC

GCGAGCTTTCTGTATAGCGGCGTGCCGAGCCGCTTTAGCGGCAGCCGCAG

CGGCACCGATTTTACCCTGACCATTAGCAGCCTGCAGCCGGAAGATTTTG

CGACCTATTATTGCCAGCAGCATTATACCACCCCGCCGACCTTTGGCCAG

GGTACCAAAGTGGAAATTAAACGAACTGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGTTAG
```

3. Amplification

The recombinant plasmids were transformed into *E. coli* TOP10. Single colonies were picked and grown on LB medium containing 100 mg/L ampicillin, at 37° C. for 16 hours under oscillation conditions. The bacteria were then collected by 8000×g centrifugation for 10 minutes. Plasmids were isolated with Tiangen endotoxin kit, dissolved in 1 ml elution EB buffer. 1.42 ml isopropanol and 0.42 ml NaCl were used to precipitate the plasmids, which were washed with 70% 0.5 ml ethanol, twice, followed by air-dry in clean bench, and dissolution in sterilizing ultrapure water (1 ml). Plasmid concentrations were measured at OD260/280. An OD260/280 value between 1.8~1.9 indicates high purity of plasmid DNA.

4. Transfection and Expression of MSBODY in Mammalian Cells 293F

Twenty-four hours prior to transfection, $1×10^6$ 293F cells were inoculated in a 125 ml flask containing 28 ml 293 freestyle medium at 37° C. with 8% $CO_2$ at 130 rpm. One hundred μl 293fectin was added to 1 ml OPtiMEM and, upon mixing, was incubated at room temperature for 5 minutes. Meanwhile, recombinant plasmids pcDNA3.1 (+) Hygro-HOKT3 single chain LDY, pcDNA3.1-Herceptin Heavy chain TKK (−) and pcDNA3.1 (+) Hygro-Herceptin light chain were admixed at a ratio of 3:2:1. The total amount of DNA quantity was 30 ug, dissolved in 1 ml OPtiMEM. Then DNA and 293fectin were fully mixed, and the total volume was 2 ml, which was incubated at room temperature for 15 minutes. The mixture was then added to the cell culture. The cells were cultured at 37° C. with 5% $CO_2$, in an incubator, at 130 rpm, for 5 days. Antibody expression in cell supernatant was detected by SDS-PAGE and western blot (FIG. 9). The antibody, referred to as MSBODY, contained a Monovalent light-chain/heavy-chain unit specific for Her2/neu, and a Single-chain unit specific for CD3.

5. Antibody Purification

The cell culture was centrifuged at 2000×g and the supernatant was collected and filtered with a 0.22 micron filtration. The collected cultured was diluted with 10 times (by volume) binding buffer (9.5 mM $NaH_2PO_4$+40.5 mM $Na_2HPO_4$, pH7.0), then purified through Sepharose Fast Flow protein A affinity chromatography column (purchased from GE company, 5 ml volume), Fab Affinity KBP Agarose High Flow Resin(purchased from ACROBiosystemscompany, 5 ml volume), and SP cation-exchanged chromatography column (purchased from GE company, 10 ml), based on manufacturer's manuals. The purified proteins were confirmed with 6% gel SDS-PAGE and coomassie blue staining (see FIG. 10).

Example 2

Analysis of Binding Activity of the Bispecific Antibody

The ability of the anti-Her2/neu-anti-CD3 bispecific antibody (MSBODY) to bind to cells having Her2 and CD3 was tested with BT474, and peripheral blood mononuclear cells (PBMC).

$3×10^5$ BT474 cells were collected from cell culture, and incubated with 50 μl 1 PBS, 10 nM Herceptin or 20 nM of the bispecific antibody. Thirty minutes later, the cells were washed twice with 1% FBS/PBS and the mixed with 2.5 μl 1 PE-labeled anti-human IgG Fc. The mixtures were incubated at room temperature for 30 minutes, and the cells were again washed with 1% FBS/PBS. The samples were then subject to examination on the FACS equipment.

Figure 11A:
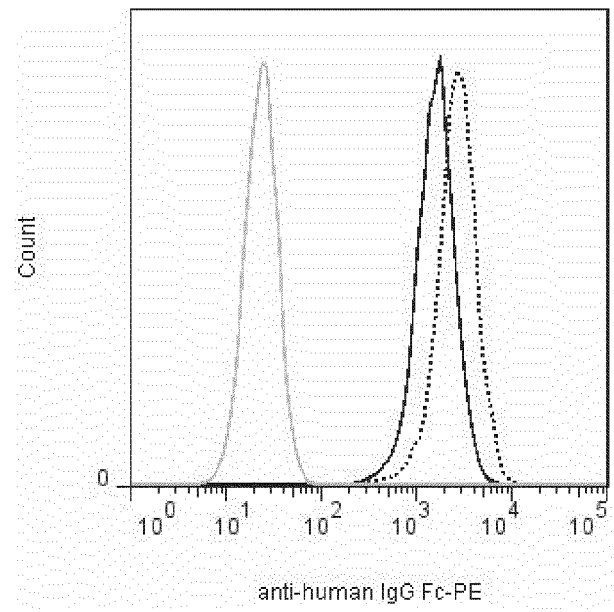

As FIG. 11A shows, both Herceptin (dark dotted line) and the bispecific antibody anti-her2Xanti-CD3 MSBODY (dark solid line) bind to breast cancer cell line BT474 wherein the gray line was negative control. This result shows that the bispecific antibody can effectively bind to Her2-expressing cancer cells.

Figure 11B:
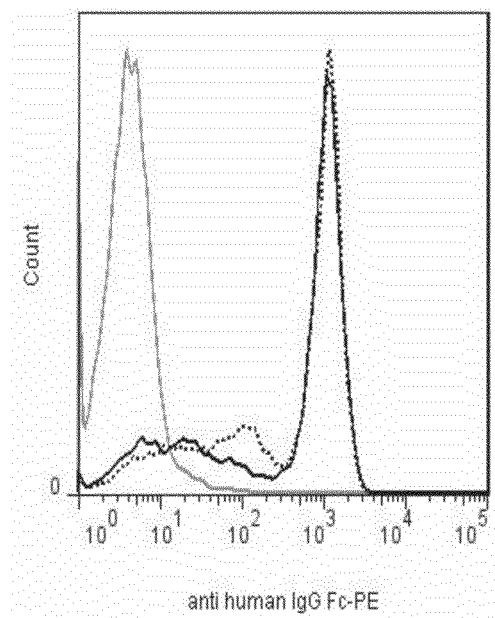

Peripheral blood mononuclear cells (PBMC) also express CD3. $1.5×10^6$ PBMC cells were prepared and incubated with 50 μl 1 PBS, 12.5 nM hOKT3 or 12.5 nM of the bispecific antibody. The abundance of PBMC cells bound by the bispecific ligand (dark solid line) was as high as by HOKT3 (dark dotted line) (FIG. 11B).

Example 3

Cytotoxicity Testing of the Bispecific Antibody

BT-474 cells, serving as target cells, were plated in a 96-well plate (10000 cells/well). Twenty-four hours later, isolated human PBMC (effector cells) were added, and the mixture was then co-incubated with a HOKT3 antibody, a MSBODY, a human IgG protein or PBS alone (40:1 effectorto-target (E-T) ratio). FIG. 12 presents images showing cell aggregation for each antibody. It is apparent that the control sample (PBS) and human IgG sample had no cell aggregation, whereas the MSBODY induced as similar amount of cell aggregation as HOKT3.

Antibody-induced cytotoxicity was measured for MSBODY, Herceptin, HOKT3, and Herceptin+HOKT3, with human IgG as control. BT-474 cells (target cell) were first stained with 5 M CFSE and then mixed with human PBMC (effector cells; E-T ratio: 5:1). Equal concentrations of Herceptin, HOKT3, Herceptin+HOKT3, MSBODY and human IgG were added into the cell culture. Following 24-hour incubation, the cells were collected and stained with 1 μg/ml PI, and were counted with flow cytometry (MoFlo XDP, Beckman Coulter). A cell was counted as dead it was dually stained with CFSE and PI. Cell death rate was measured as the ratio between dead cells and total cells. The cytotoxicity was calculated as the difference between the measured cell death rate and natural cell death rate. The results were shown in FIG. 13 which shows that MSBODY resulted in the highest cytotoxicity, as compared to Herceptin and HOKT3, even to the combination of Herceptin and HOKT3.

Another cytotoxicity study was performed with human T lymphocyte as the effector cell and BT-474 as the target cell. BT-474 cells were first stained with 5 μM CFSE. The next day, human PBMC were mixed with 50 nM human IgG, Herceptin+HOKT3, MSBODY, or PBS, at room temperature for 30 minutes. The cells were then washed twice with 1% FBS-PBS, and then resuspended in 20% FBS. The treated PBMC cells were then added to BT-474 cells, at E-T ratios of: 20:1, 10:1, 5:1, 2.5:1 and 1.25:1. The mixed cells were incubated for 48 hours (FIG. 14). Subsequently, the collected cells were stained and counted. As shown in FIG. 14, MSBODY-incubated PBMC led to the most cell death, as compared to PBMC that were pre-mixed with Herceptin and HOKT3.

This example, therefore, shows unexpectedly that MSBODY is as effective as HOKT3 in causing cell aggregation and causes higher cytotoxicity than both Herceptin and HOKT3.

Example 4

Comparison Between Antibodies

This example compares the MSBODY with other types of antibodies that have specificity to either or both Her2/neu and CD3, and shows the unexpectedly high activity and stability of the MSBODY.

Figure 15A:
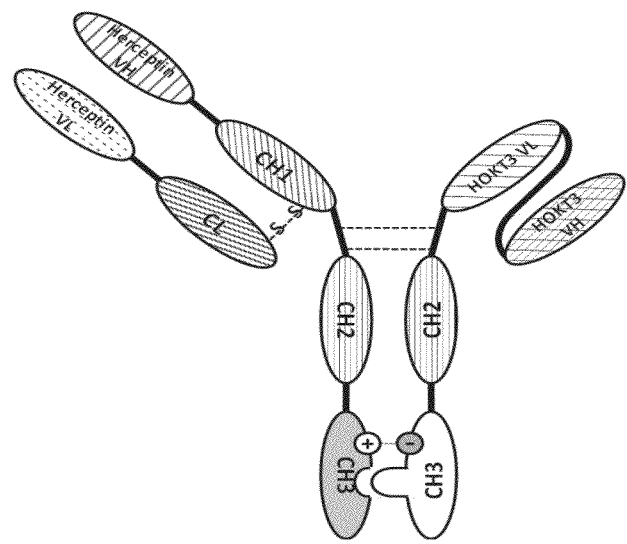
Figure 15B:
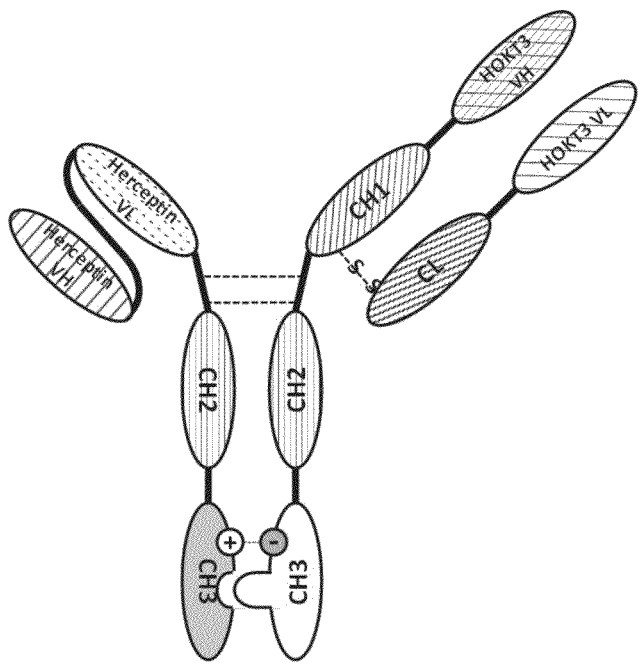

The various types of antibodies tested in this example are illustrated in FIG. 15A-E. FIG. 15A shows a MSBODY in which the monovalent unit has Herceptin's VH and VL, and the single-chain unit includes HOKT3's VH and VL. The antibody in FIG. 15B is almost the mirror image of the MSBODY, termed "SMBODY". The SMBODY has a monovalent unit containing the VH and VL of HOKT3, and a single-chain unit having Herceptin's VH and VL.

Figure 15C:
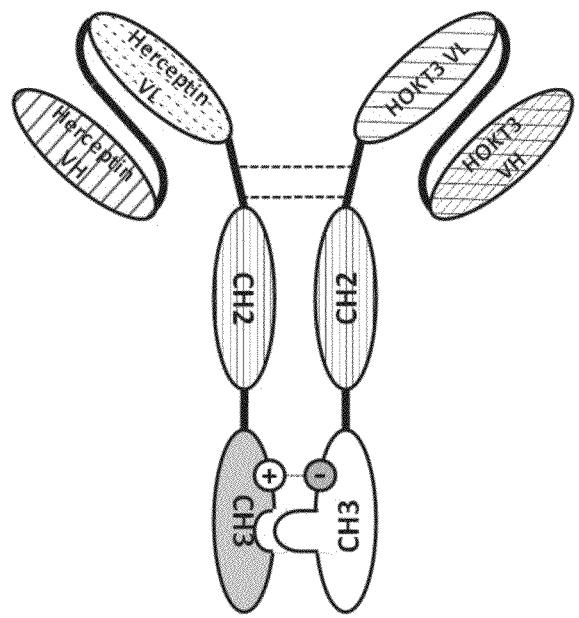

The antibody in FIG. 15C, referred to as "SSBODY", contains two single-chain units, one having Herceptin's VH and VL and the other having HOKT3's VH and VL. All of MSBODY, SMBODY and SSBODY, as shown in the figures, contain the optional salt bridge and knob in the hole.

Figure 15D:
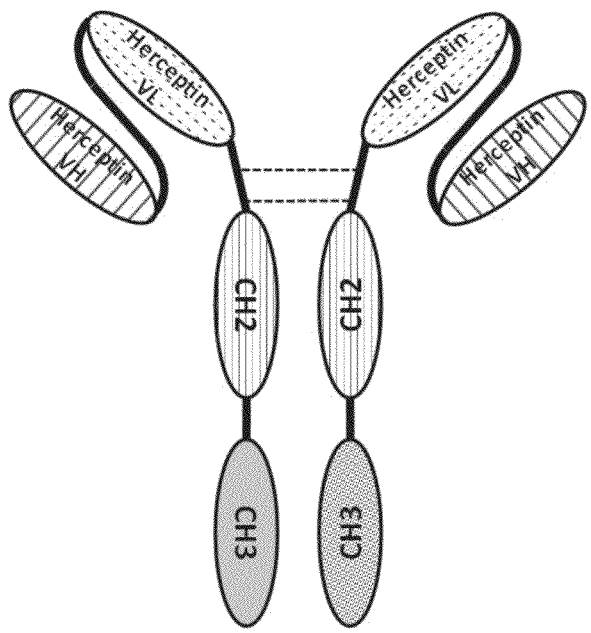
Figure 15E:
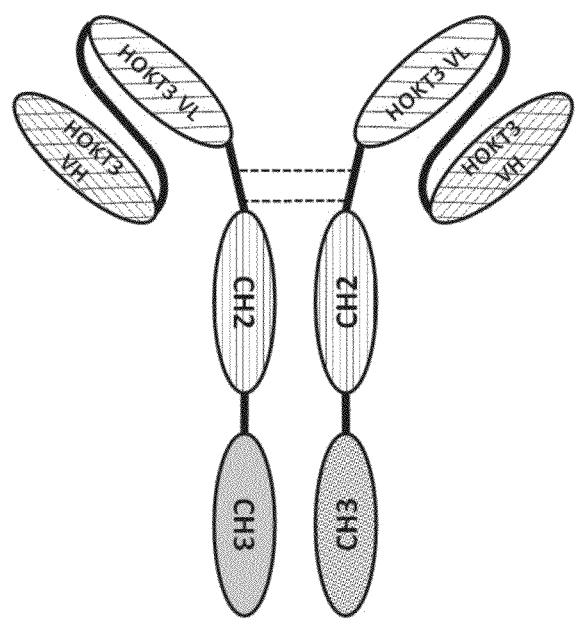

FIG. 15D illustrates a dual-single-chain antibody (referred as "Herceptin single-chain"), with both single-chain units containing Herceptin's VH and VL. This antibody, there, has a single specificity. Finally, FIG. 15E shows a dual-single-chain antibody having two single-chain units containing HOKT3's VH and VL, which is referred to as "HOKT3 single-chain" throughout.

To compare the binding affinity of MSBODY and SMBODY to Her2 expressing cells, $3 \times 10^5$ BT-474 cells were incubated with various dilutions of purified MSBODY or SMBODY in 50 μl of Dulbecco's PBS+1% Fetal Bovine Serum (1% FBS-PBS) for 30 minutes at room temperature (RT) with gentle mixing. Cells were then washed two times in 1% FBS-PBS and incubated for 30 minutes in 50 μl of 1% FBS-PBS containing 10 μg/ml PE conjugated mouse anti-human IgG Fc antibody (Biolegend, 409304). Cells were again washed twice, re-suspended in 1% FBS-PBS, and subjected to flow cytometry.

BT-474 cells used in the described binding assay were analyzed by flow cytometry (MoFlo XDP, Beckman Coulter) to detect cell-bound antibody (FIGS. 16A and B). Values and graphical analysis were generated using (GraphPad Prism 5). The determined mean fluorescence intensity was plotted as a function of the antibody concentration to determine Kd by the One Site Binding (hyperbola) method. The results are presented in FIG. 17, which show that MSBODY had about 2 times higher affinity than SMBODY at binding to Her2-expressing cells.

The thermal stability of MSBODY, as compared to SMBODY and various single-chain antibodies, was measured with a thermal challenge assay. Herceptin, Herceptin single-chain, MSBODY and SSBODY were diluted to 0.5 mg/mL and placed at various temperatures ranging from 37° C. to 82° C. (5° C. steps) for one hour.

Her2 proteins (2.5 μg/ml), incubated at 4° C. overnight were treated with 3% F BS for 2 hours. After 3 washes with PBST, the antibodies were diluted to 1 nM and reacted with Her2 for 1 hour. Subsequently, anti-human IgG Fc-HRP (1:10K) were added and kept at reacting temperature for half an hour. The samples were then washed five times with PBST and stained with TMB, which was read at OD 450. FIG. 18 shows the thermal challenge curves. The Y-axis temperature, T50, indicates the temperature at which 50% of antibody retained binding ability to Her2 following the thermal challenge. The binding profiles were normalized to 100% maximum binding. It is shown that the MSBODY retains much higher thermal stability than SMBODY, SSBODY and Herceptin single-chain antibody, which is close to that of full size Herceptin. This result is quite unexpected since single-chain antibodies were known to be unstable.

Antibody-induced cytotoxicity was measured for MSBODY and SMBODY, with human IgG as control. Her2-high BT-474 cells that express relatively high level of Her2 protein, and Her2-low cells such as MCF-7 and MDA-MB-231 that express relatively low level of Her2 protein, were first stained with 5 μM CFSE and then mixed with human PBMC (effector cells; E-T ratio: 5:1). Equal concentrations of MSBODY, SMBODY and human IgG were added into the cell culture. Following 48-hour incubation, the cells were collected and stained with 1 μg/ml PI, and were counted with flow cytometry (MoFlo XDP, Beckman Coulter). A cell was counted as dead when it was dually stained with CFSE and PI. Cell death rate was measured as the ratio between dead cells and total cells. The cytotoxicity was calculated as the difference between the measured cell death rate and natural cell death rate. The results were shown in FIG. 19 which shows that both MSBODY and SMBODY resulted in similar cytotoxicity against Her2-high BT474 cells. However, the MSBODY showed significantly higher cytotoxicity to Her2-low breast cancer cell lines such as MCF-7 and MDA-MB-231.

Example 5

Preparation of Other Monovalent Single-Chain Bispecific Antibodies

The above examples show the preparation and testing of a specific monovalent single-chain bispecific antibody (MS-BODY), which includes a monovalent unit specific for Her2/neu and a single-chain unit for CD3. Using similar methods, additional such MSBODY can be prepared and used, each having a monovalent unit recognizing a tumor cell and a single-chain unit recognizing an effector cell.

For instance, one MSBODY can include a monovalent unit containing a modified light chain and heavy chain of an antibody such as rituximab, an anti-AC133 antibody and cetuximab. The heavy chain and light chain sequences of rituximab sequence are provided in the table below.

TABLE 10

Heavy chain of rituximab
(SEQ ID NO: 47)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSAASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

Light chain of rituximab
(SEQ ID NO: 48)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

The heavy chain and light chain sequences of an anti-AC133 antibody sequence are provided in the table below.

TABLE 11

Heavy chain of anti-AC133 antibody
(SEQ ID NO: 49)
QVQLQQSGAELVRPGASVKLSCKASGYTFSDIHEMHWVKQTPVHGLEWIGD

IDPGTGDTAYNLKFKGKATLTTDKSSSTAYMELRSLTSEDSAVYYCTLGA

FVYWGQGTLVTVSAASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

TABLE 11-continued

SRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK

Light chain of anti-AC133 antibody
(SEQ ID NO: 50)
DVVVTQTPLSLPVSFGDQVSISCRSSQSLANSYGNTYLSWYLHKPGQSPQ

LLIYGISNRFSGVPDRFSGSGSGTDFTLKISTIKPEDLGMYYCLQGTHQP

YTFUGGTKLEIKRTVAAPSVFIFPPSDEQLKSGTASVVCLLNNFIPREAK

VQWKVDNALQSGNSQESVTEQDSKDSTYSLSSTLTLSKADYEKHKVYACE

VTHQGLSSPVTKSFNRGEC

The heavy chain and light chain sequences of cetuximab are provided in the table below.

TABLE 12

Heavy chain of cetuximab
(SEQ ID NO: 51)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLEPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

Light chain of cetuximab
(SEQ ID NO: 52)
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNEYPREAKVQWKV

DNALQSGNSQESVTEQDSKDSTYSLSSTLTLSKADYEKHKVYACEVTHQG

LSSPVTKSFNRGEC

Each of the heavy chains as illustrated above can be modified to introduce a salt-bridge and/or a knob into the hole. Examples of such modifications are provided in Tables 1-3.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. An antibody comprising:
    (a) a monovalent unit comprising a light chain-heavy chain pair having specificity to Her2, wherein the light chain of the monovalent unit comprises SEQ ID NO: 5, and wherein the heavy chain of the monovalent unit comprises SEQ ID NO: 3; and
    (b) a single-chain unit comprising a fusion peptide comprising a single-chain variable fragment (scFv) having specificity to CD3 and an Fc fragment comprising a CH2 domain and a CH3 domain, wherein the fusion peptide comprises SEQ ID NO: 1.

2. The antibody of claim 1, wherein the light chain is bound to the heavy chain through a disulfide bond.

3. The antibody of claim 1, wherein the heavy chain is bound to the fusion peptide through one or more disulfide bonds.

4. The antibody of claim 1, wherein the antibody is a humanized antibody.

5. The antibody of claim 1, further comprising a detectable label.

6. The antibody of claim 1, wherein the antibody binds Her2 expressing breast cancer cells and one or more CD3 expressing cells selected from the group consisting of a lymphocyte, a monocyte and a macrophage.

7. The antibody of claim 1, wherein the Fc region of one unit has the following amino acid substitutions: Threonine (T) to Tryptophan (W) substitution at position 366, Lysine (K) to Aspartic acid (D) substitution at position 392, and Lysine (K) to Aspartic acid (D) substitution at position 409 (Kabat numbering system); and
    wherein the Fc region of the other unit has the following amino acid substitutions: Leucine (L) to Arginine (R) substitution at position 368, Aspartic acid (D) to Lysine (K) substitution at position 399, and Tyrosine (Y) to Alanine (A) substitution at position 407 (Kabat numbering system).

8. The antibody of claim 1, wherein the Fc region of the heavy chain of the monovalent unit has the following amino acid substitutions: Threonine (T) to Tryptophan (W) substitution at position 366, Lysine (K) to Aspartic acid (D) substitution at position 392, and Lysine (K) to Aspartic acid (D) substitution at position 409 (Kabat numbering system); and
   wherein the Fc region of the fusion peptide has the following amino acid substitutions: Leucine (L) to Arginine (R) substitution at position 368, Aspartic acid (D) to Lysine (K) substitution at position 399, and Tyrosine (Y) to Alanine (A) substitution at position 407 (Kabat numbering system).

* * * * *